US010286201B2

(12) United States Patent
McKinnon et al.

(10) Patent No.: US 10,286,201 B2
(45) Date of Patent: May 14, 2019

(54) CONNECTION APPARATUS FOR A MEDICAL DEVICE

(71) Applicant: Becton Dickinson and Company Limited, Dun Laoghaire (IE)

(72) Inventors: Austin McKinnon, Ringwood, NJ (US); Laurie Sanders, Glen Ridge, NJ (US); Yan Yevmenenko, New York, NY (US); Jude Cancellieri, Oakland, NJ (US); Daniel Hamilton, Mont Vernon, MA (US); James J. Kennedy, III, Mont Vernon, MA (US); Lai Chiu Tang, Cambridge (GB); Richard Mann, Cambridge (GB)

(73) Assignee: Becton Dickinson and Company Limited, Dun Laoghaire (IE)

( * ) Notice: Subject to any disclaimer, the term of this patent is extended or adjusted under 35 U.S.C. 154(b) by 323 days.

(21) Appl. No.: 14/532,177

(22) Filed: Nov. 4, 2014

(65) Prior Publication Data

US 2016/0136412 A1 May 19, 2016

Related U.S. Application Data

(60) Provisional application No. 61/900,661, filed on Nov. 6, 2013.

(51) Int. Cl.
*A61M 39/10* (2006.01)
(52) U.S. Cl.
CPC . *A61M 39/1011* (2013.01); *A61M 2039/1033* (2013.01); *A61M 2039/1044* (2013.01); *A61M 2039/1072* (2013.01)

(58) Field of Classification Search
CPC .. A61M 2039/1033; A61M 2039/1044; A61M 39/10
See application file for complete search history.

(56) References Cited

U.S. PATENT DOCUMENTS

| 2,290,403 | A | 7/1942 | Wyss |
| 3,667,636 | A | 6/1972 | Landen |
| 4,436,125 | A | 3/1984 | Blenkush |
| 4,564,054 | A | 1/1986 | Gustavsson |
| 4,673,404 | A | 6/1987 | Gustavsson |

(Continued)

FOREIGN PATENT DOCUMENTS

| CA | 1205836 A | 6/1986 |
| DE | 9320713 U1 | 3/1995 |

(Continued)

*Primary Examiner* — Deanna K Hall
(74) *Attorney, Agent, or Firm* — The Webb Law Firm

(57) ABSTRACT

A connection apparatus for a medical device includes a first connection member having a first end and a second end with the first connection member defining at least one channel adjacent the first end. The at least one channel having a first portion extending in an axial direction and a shoulder adjacent to the first end of the first connection member that defines a channel entry. The at least one channel having a second portion extending in a transverse direction relative to the axial direction. The connection apparatus further including a second connection member having a first end and a second end and at least one protrusion adjacent the first end. The shoulder is configured to guide the at least one protrusion of the second connection member into the channel entry regardless of the orientation of the at least one protrusion relative to the channel entry.

19 Claims, 15 Drawing Sheets

(56) References Cited

U.S. PATENT DOCUMENTS

| | | |
|---|---|---|
| 4,932,937 A | 6/1990 | Gustavsson et al. |
| 5,052,725 A | 10/1991 | Meyer et al. |
| 5,104,158 A | 4/1992 | Meyer et al. |
| 5,122,129 A | 6/1992 | Olson et al. |
| 5,280,876 A | 1/1994 | Atkins |
| 5,290,254 A | 3/1994 | Vaillancourt |
| 5,322,518 A | 6/1994 | Schneider et al. |
| 5,334,188 A | 8/1994 | Inoue et al. |
| 5,360,011 A | 11/1994 | McCallister |
| 5,395,348 A | 3/1995 | Ryan |
| 5,437,650 A | 8/1995 | Larkin et al. |
| 5,464,123 A | 11/1995 | Scarrow |
| 5,472,430 A | 12/1995 | Vaillancourt et al. |
| 5,478,328 A | 12/1995 | Silverman et al. |
| 5,487,728 A | 1/1996 | Vaillancourt |
| 5,507,733 A | 4/1996 | Larkin et al. |
| 5,509,911 A | 4/1996 | Cottone, Sr. et al. |
| 5,545,152 A | 8/1996 | Funderburk et al. |
| 5,607,392 A | 3/1997 | Kanner |
| 5,609,584 A | 3/1997 | Gettig et al. |
| 5,611,792 A | 3/1997 | Gustafsson |
| 5,647,845 A | 7/1997 | Haber et al. |
| 5,685,866 A | 11/1997 | Lopez |
| 5,807,347 A | 9/1998 | Bonaldo |
| 5,897,526 A | 4/1999 | Vaillancourt |
| 6,063,068 A | 5/2000 | Fowles et al. |
| 6,089,541 A | 7/2000 | Weinheimer et al. |
| 6,113,583 A | 9/2000 | Fowles et al. |
| 6,132,404 A | 10/2000 | Lopez |
| 6,139,534 A | 10/2000 | Niedospial, Jr. et al. |
| 6,221,041 B1 | 4/2001 | Russo |
| 6,221,056 B1 | 4/2001 | Silverman |
| 6,336,914 B1* | 1/2002 | Gillespie, III .... A61M 25/0606 604/165.01 |
| 6,343,629 B1 | 2/2002 | Wessman et al. |
| 6,358,236 B1 | 3/2002 | DeFoggi et al. |
| 6,409,708 B1 | 6/2002 | Wessman |
| 6,474,375 B2 | 11/2002 | Spero et al. |
| 6,478,788 B1 | 11/2002 | Aneas |
| 6,544,246 B1 | 4/2003 | Niedospial, Jr. |
| 6,551,299 B2 | 4/2003 | Miyoshi et al. |
| 6,585,695 B1 | 7/2003 | Adair et al. |
| 6,599,273 B1 | 7/2003 | Lopez |
| 6,610,040 B1 | 8/2003 | Fowles et al. |
| 6,629,958 B1 | 10/2003 | Spinello |
| 6,656,433 B2 | 12/2003 | Sasso |
| 6,715,520 B2 | 4/2004 | Andreasson et al. |
| 6,814,726 B1 | 11/2004 | Lauer |
| 6,852,103 B2 | 2/2005 | Fowles et al. |
| 6,875,203 B1 | 4/2005 | Fowles et al. |
| 6,875,205 B2 | 4/2005 | Leinsing |
| 6,911,025 B2 | 6/2005 | Miyahara |
| 6,997,917 B2 | 2/2006 | Niedospial, Jr. et al. |
| 7,040,598 B2 | 5/2006 | Raybuck |
| 7,083,605 B2 | 8/2006 | Miyahara |
| 7,097,209 B2 | 8/2006 | Unger et al. |
| 7,261,707 B2 | 8/2007 | Frezza et al. |
| 7,306,584 B2 | 12/2007 | Wessman et al. |
| 7,326,194 B2 | 2/2008 | Zinger et al. |
| 7,350,535 B2 | 4/2008 | Liepold et al. |
| 7,354,427 B2 | 4/2008 | Fangrow |
| 7,452,349 B2 | 11/2008 | Miyahara |
| 7,547,300 B2 | 6/2009 | Fangrow |
| 7,628,772 B2 | 12/2009 | McConnell et al. |
| 7,648,491 B2 | 1/2010 | Rogers |
| 7,658,734 B2 | 2/2010 | Adair et al. |
| 7,743,799 B2 | 6/2010 | Mosler et al. |
| 7,744,581 B2 | 6/2010 | Wallen et al. |
| 7,758,560 B2 | 7/2010 | Connell et al. |
| 7,803,140 B2 | 9/2010 | Fangrow, Jr. |
| 7,867,215 B2 | 1/2011 | Akerlund et al. |
| 7,879,018 B2 | 2/2011 | Zinger et al. |
| 7,900,659 B2 | 3/2011 | Whitley et al. |
| 7,927,316 B2 | 4/2011 | Proulx et al. |
| 7,942,860 B2 | 5/2011 | Horppu |
| 7,975,733 B2 | 7/2011 | Horppu et al. |
| 8,096,525 B2 | 1/2012 | Ryan |
| 8,122,923 B2 | 2/2012 | Kraus et al. |
| 8,123,738 B2 | 2/2012 | Vaillancourt |
| 8,137,332 B2 | 3/2012 | Pipelka |
| 8,167,863 B2 | 5/2012 | Yow |
| 8,177,768 B2 | 5/2012 | Leinsing |
| 8,196,614 B2 | 6/2012 | Kriheli |
| 8,206,367 B2 | 6/2012 | Warren et al. |
| 8,211,069 B2 | 7/2012 | Fangrow, Jr. |
| 8,226,628 B2 | 7/2012 | Muramatsu et al. |
| 8,257,286 B2 | 9/2012 | Meyer et al. |
| 8,267,127 B2 | 9/2012 | Kriheli |
| 8,277,424 B2 | 10/2012 | Pan |
| 8,317,741 B2 | 11/2012 | Kraushaar |
| 8,317,743 B2 | 11/2012 | Denenburg |
| 8,398,607 B2 | 3/2013 | Fangrow, Jr. |
| 8,403,905 B2 | 3/2013 | Yow |
| 8,425,487 B2 | 4/2013 | Beiriger et al. |
| 8,449,521 B2 | 5/2013 | Thorne, Jr. et al. |
| 8,454,579 B2 | 6/2013 | Fangrow, Jr. |
| 2003/0070726 A1 | 4/2003 | Andreasson et al. |
| 2005/0065495 A1 | 3/2005 | Zambaux |
| 2005/0182383 A1 | 8/2005 | Wallen |
| 2005/0215976 A1 | 9/2005 | Wallen |
| 2007/0079894 A1 | 4/2007 | Kraus et al. |
| 2008/0045919 A1 | 2/2008 | Jakob et al. |
| 2008/0287914 A1 | 11/2008 | Wyatt et al. |
| 2008/0287919 A1 | 11/2008 | Kimball |
| 2009/0159485 A1 | 6/2009 | Jakob et al. |
| 2010/0179506 A1 | 7/2010 | Shemesh et al. |
| 2010/0217226 A1 | 8/2010 | Shemesh |
| 2011/0004183 A1 | 1/2011 | Carrez et al. |
| 2011/0062703 A1 | 3/2011 | Lopez et al. |
| 2011/0074148 A1 | 3/2011 | Imai |
| 2011/0106046 A1 | 5/2011 | Hiranuma et al. |
| 2011/0257621 A1 | 10/2011 | Fangrow |
| 2011/0291406 A1 | 12/2011 | Kraft et al. |
| 2012/0035580 A1 | 2/2012 | Fangrow |
| 2012/0046636 A1 | 2/2012 | Kriheli |
| 2012/0123381 A1 | 5/2012 | Kraus et al. |
| 2012/0192968 A1 | 8/2012 | Bonnal et al. |
| 2012/0192976 A1 | 8/2012 | Rahimy et al. |
| 2012/0203193 A1 | 8/2012 | Rogers |
| 2012/0265163 A1 | 10/2012 | Cheng et al. |
| 2012/0279884 A1 | 11/2012 | Tennican et al. |
| 2012/0316536 A1* | 12/2012 | Carrez ............... A61M 39/1011 604/535 |
| 2013/0006211 A1 | 1/2013 | Takemoto |
| 2013/0012908 A1 | 1/2013 | Yeung |
| 2013/0066293 A1 | 3/2013 | Garfield et al. |
| 2013/0072893 A1 | 3/2013 | Takemoto |
| 2013/0076019 A1 | 3/2013 | Takemoto |
| 2013/0079744 A1 | 3/2013 | Okiyama et al. |

FOREIGN PATENT DOCUMENTS

| | | |
|---|---|---|
| DE | 19847215 A1 | 4/2000 |
| EP | 2462971 A1 | 6/2012 |
| EP | 2813257 A1 | 12/2014 |
| FR | 2058576 | 9/1969 |
| FR | 2978353 A1 | 2/2013 |
| GB | 2451891 A | 2/2009 |
| WO | 2005011781 A1 | 2/2005 |
| WO | 2006103074 A1 | 10/2006 |
| WO | 2009024807 A1 | 2/2009 |
| WO | 2009090627 A1 | 7/2009 |
| WO | 2011050333 A1 | 4/2011 |
| WO | 2012069401 A1 | 5/2012 |
| WO | 2012119225 A1 | 9/2012 |
| WO | 2012168235 A1 | 12/2012 |
| WO | 2013025946 A1 | 2/2013 |
| WO | 2013054323 A1 | 4/2013 |
| WO | 2013066779 A1 | 5/2013 |
| WO | 2013115730 A1 | 8/2013 |
| WO | 2013179596 A1 | 12/2013 |

* cited by examiner

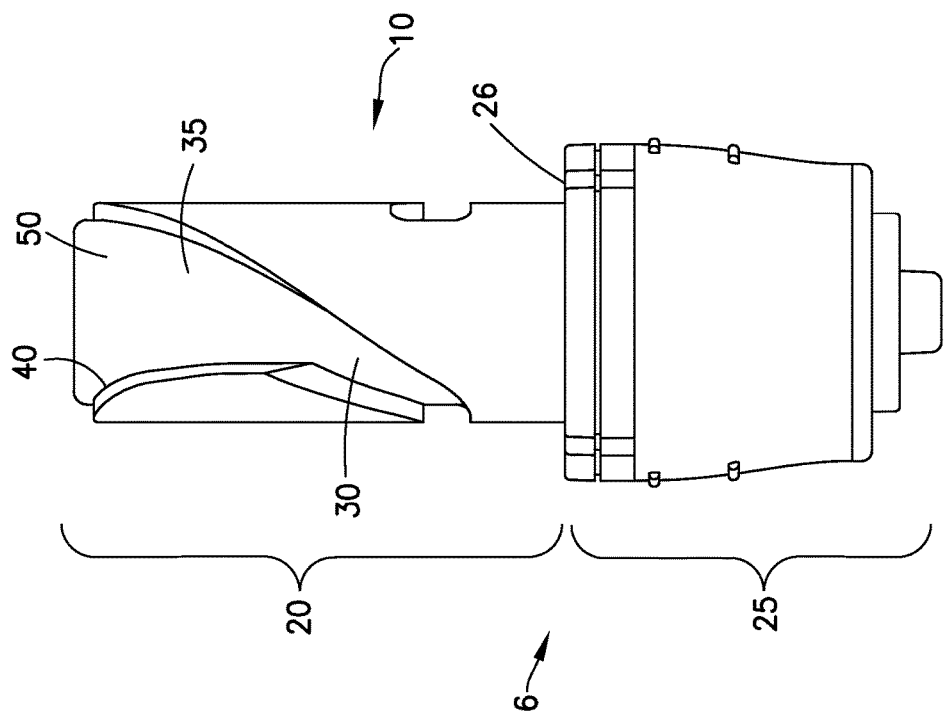
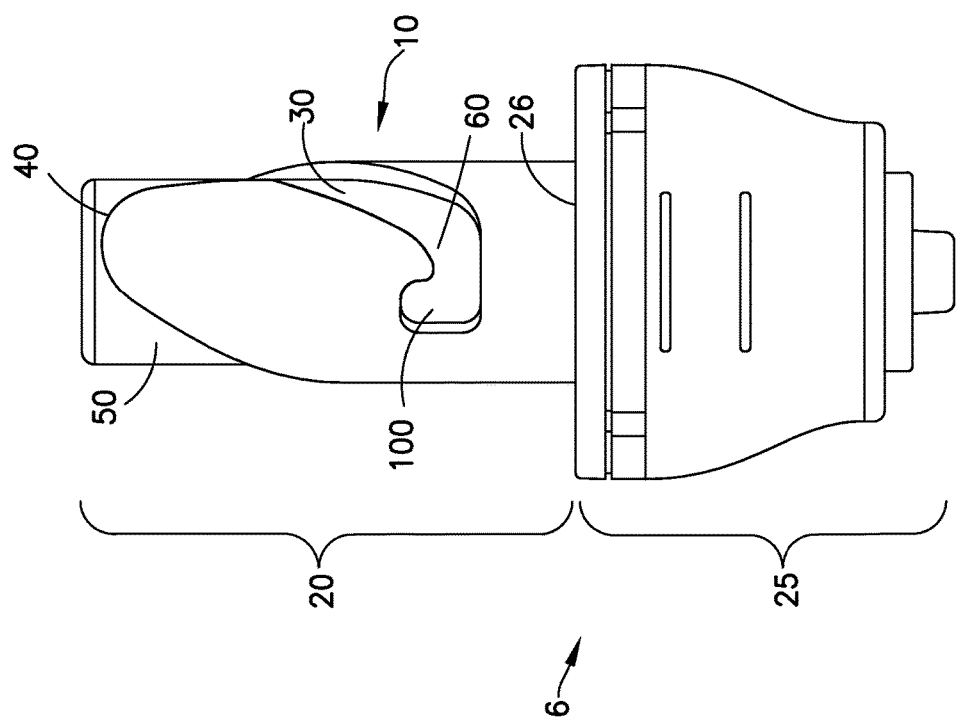

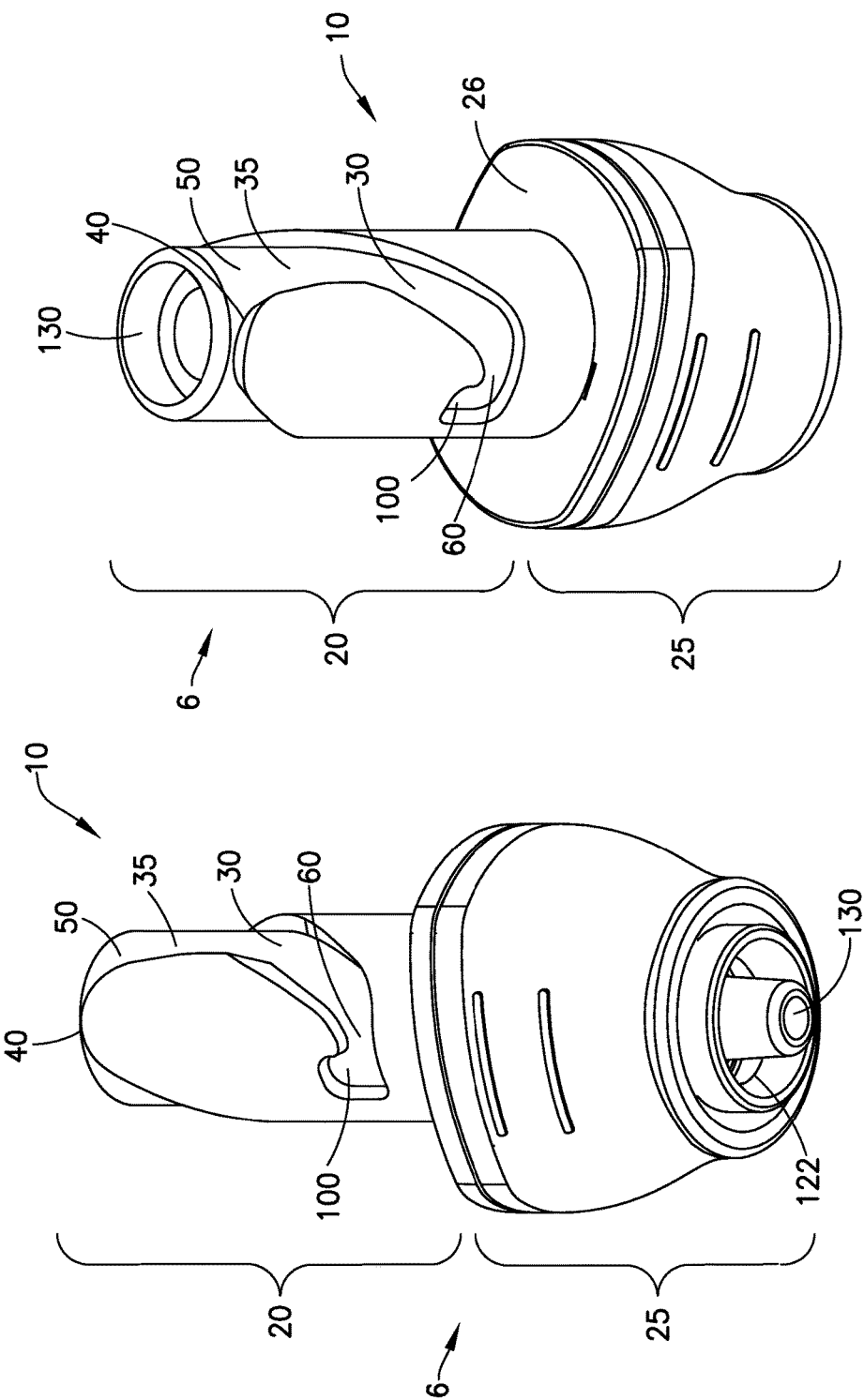

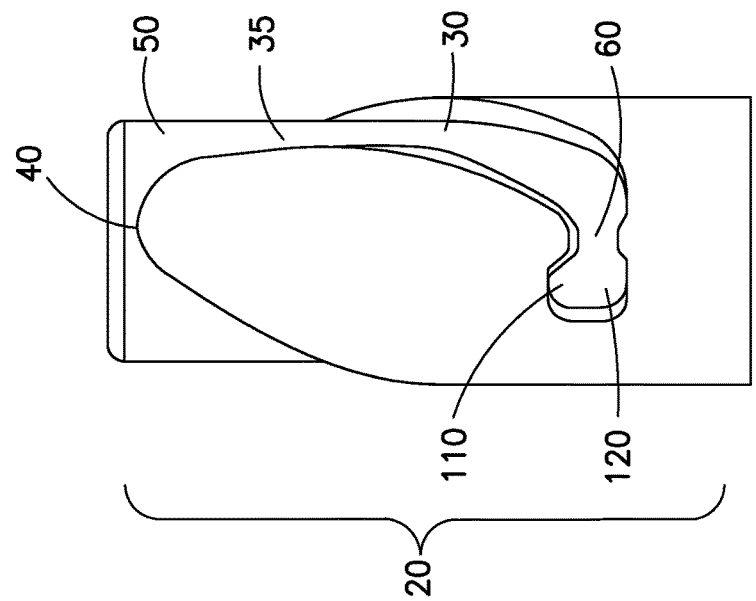
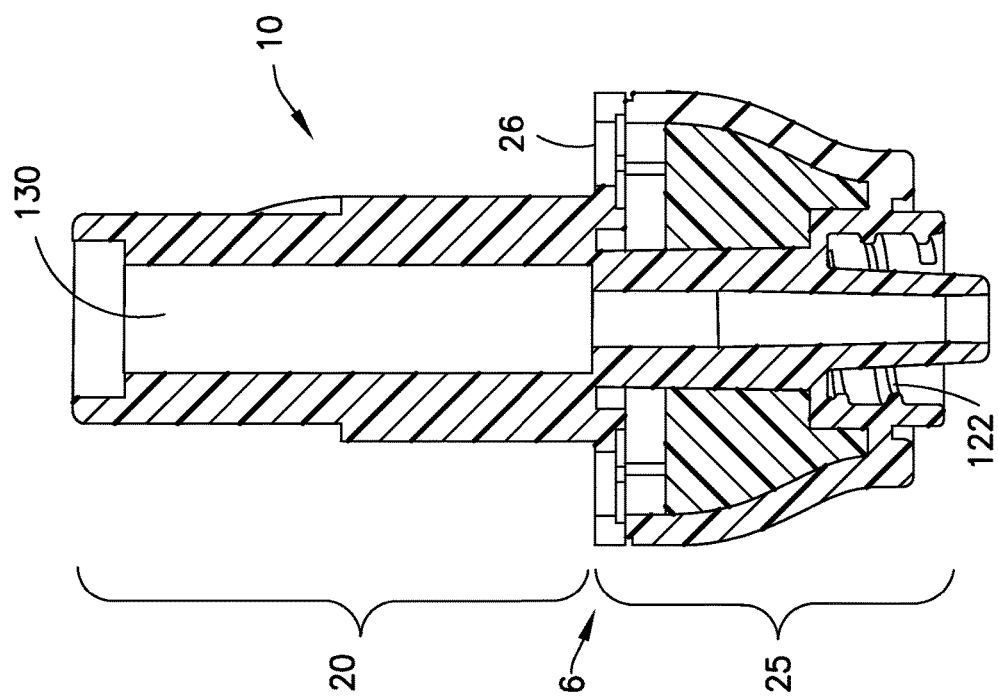
FIG. 7A
FIG. 6

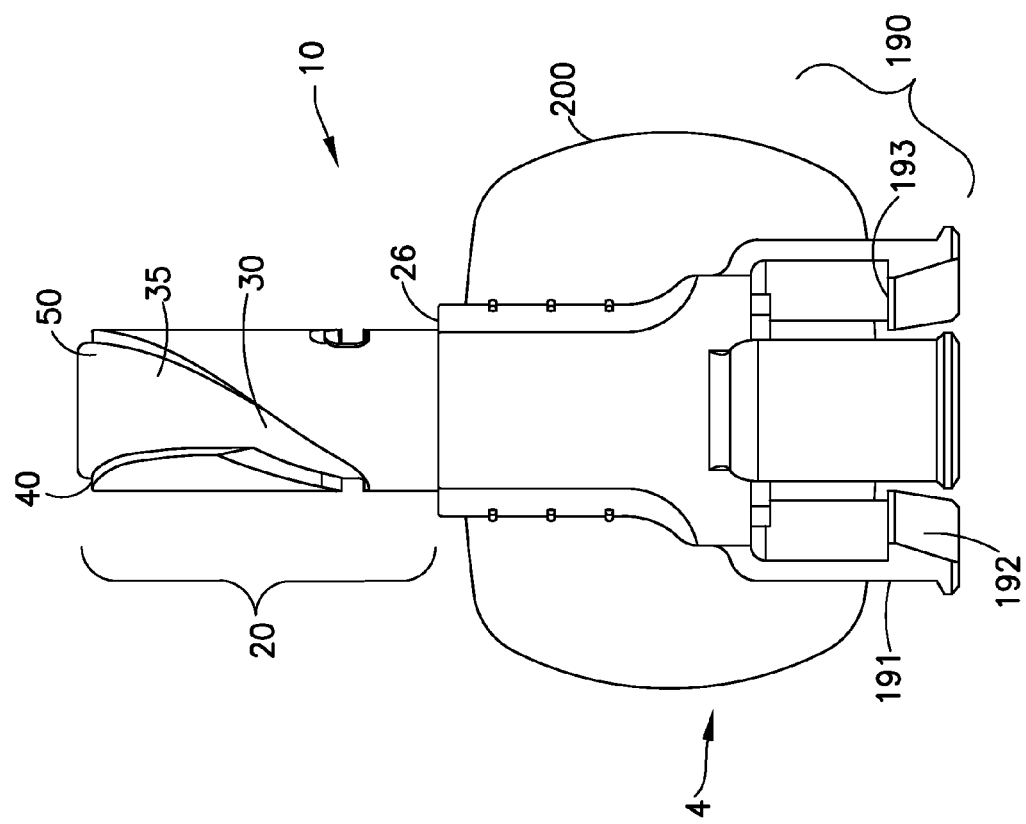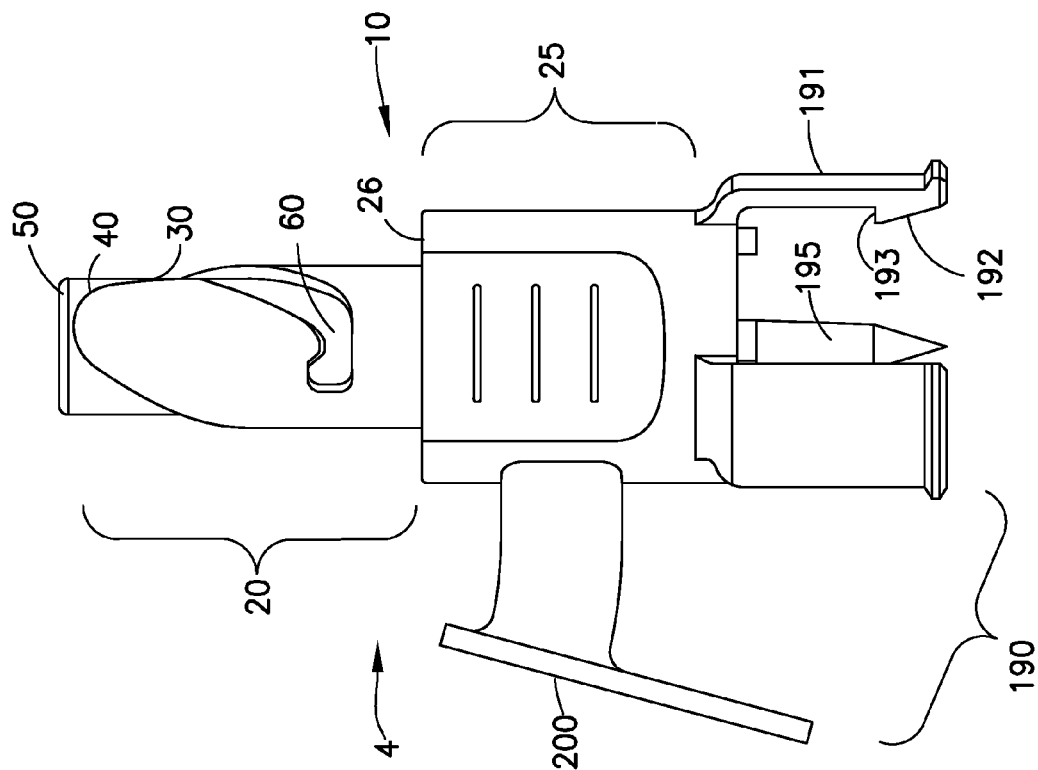

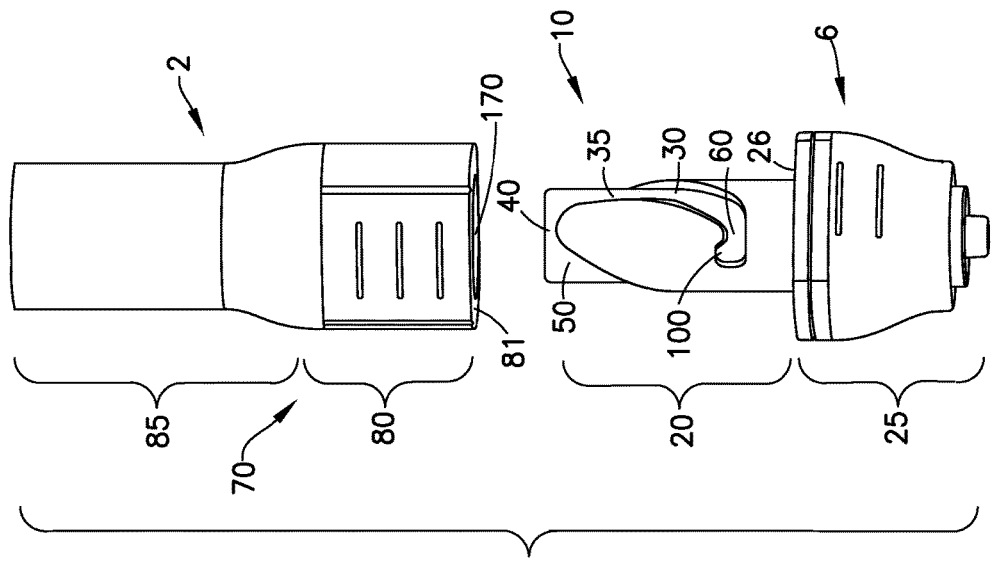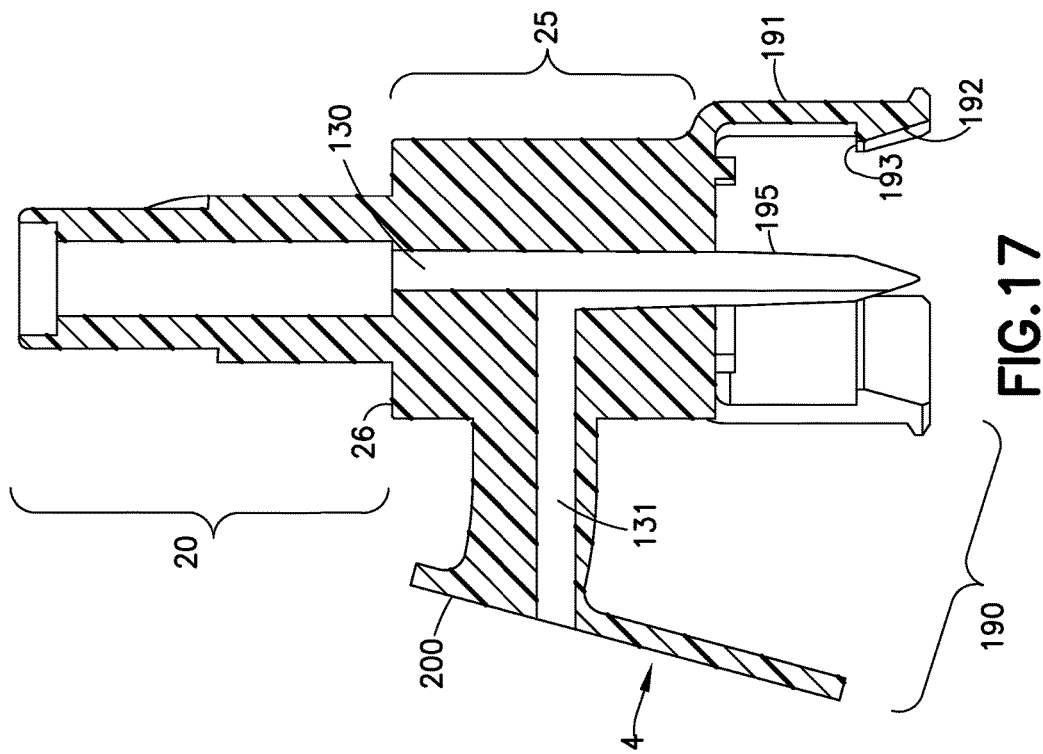

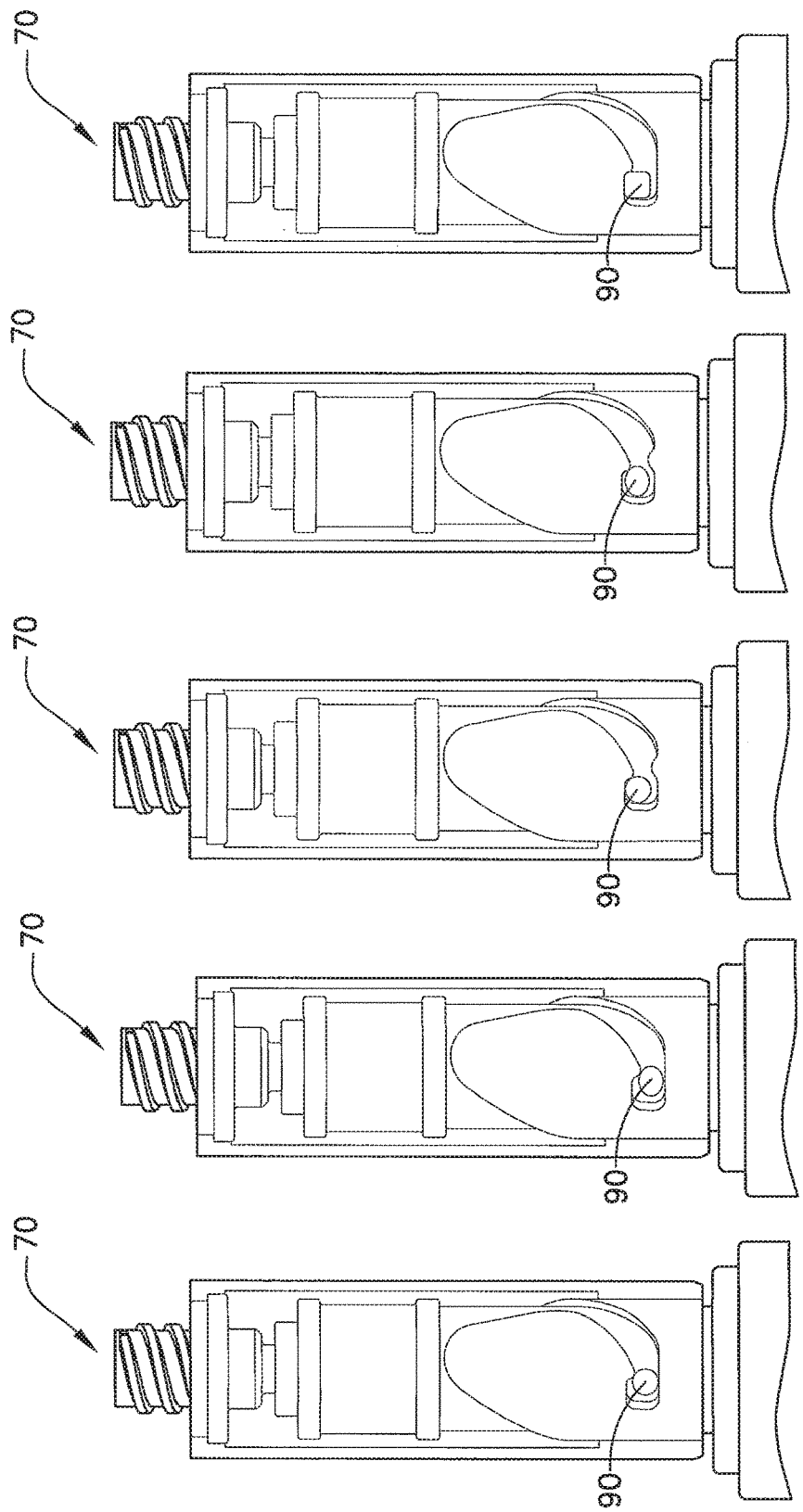

CONNECTION APPARATUS FOR A MEDICAL DEVICE

CROSS-REFERENCE TO RELATED APPLICATION

This application claims priority to U.S. Provisional Application Ser. No. 61/900,661, filed Nov. 6, 2013, which is hereby incorporated by reference in its entirety.

BACKGROUND OF THE INVENTION

Field of the Invention

The present application relates to a connection apparatus for a medical device. More specifically, the present application relates to connection members for closed system transfer devices (CSTDs), including connection members that can mate and lock together two connection members of a CSTD.

Description of Related Art

The treatment of many conditions, disorders, and diseases involves the administration of toxic compounds. For example, treatment of certain kidney disorders often involves administration of cyclophosphamide, an alkylating agent. While the side-effects of cyclophosphamide treatment are well known and expected in patients who receive this treatment, healthcare practitioners who administer cyclophosphamide also face a risk of exposure during reconstitution of the drug and subsequent administration to the patient.

Devices for reconstitution and subsequent administration of toxic compounds, known as closed system transfer devices (CSTDs), are known in the art. Generally, these devices include an adapter for connection to a vial containing the powdered or lyophilized compound, an adapter on a syringe, and an adapter on a conduit providing fluid access to the patient's circulatory system. Typically, the healthcare practitioner will reconstitute the powdered or lyophilized compound with saline or some other reconstitution medium by attaching the syringe to the vial via connection of the respective adapters, reconstitute the drug, aspirate the compound into the syringe, disconnect the adapters, and then attach the syringe to the fluid conduit through the respective adapters for administration to the patient.

Inherent in the typical CSTD is the need to connect and disconnect the various adapters in order to reconstitute and administer the drug. Such repeated connection and disconnection increases the risk of accidents and exposure to the toxic compounds. The issue of safety in administration of these compounds is one that has been identified as being of critical importance by professional organizations and government agencies alike.

SUMMARY OF THE INVENTION

In one aspect, a connection apparatus for a medical device includes a first connection member having a first end and a second end with the first connection member defining at least one channel adjacent the first end. The at least one channel has a first portion extending in an axial direction and a shoulder adjacent to the first end of the first connection member that defines a channel entry. The at least one channel having a second portion extending in a transverse direction relative to the axial direction. The connection apparatus also includes a second connection member having a first end and a second end with the second connection member having at least one protrusion adjacent the first end. When the at least one protrusion of the second connection member enters the at least one channel of the first connection member, axial movement of the second connection member towards the first connection member causes at least one of the first and second connection members to rotate relative to the other connection member to enter a locked state, wherein the shoulder is configured to guide the at least one protrusion of the second connection member into the channel entry regardless of the orientation of the at least one protrusion relative to the channel entry.

The channel entry may be wider than the first portion of the at least one channel and the second portion of the at least one channel. The second portion of the at least one channel may include a notch extending in the axial direction. The notch may extend towards the first end of the first connection member. In other aspects, the notch may extend towards the second end of the first connection member relative to the second portion of the at least one channel. The at least one protrusion may form a positive lock with the notch to removably secure the first connection member to the second connection member when the first and second connection members are in the locked state. The second portion of the at least one channel may be a substantially axial notch extending distally and a substantially axial notch extending proximally relative to the first end of the first connection member.

The first and second connection members may include fluid channels therethrough such that when the first connection member and second connection member are mated, the fluid channels form a fluid path. At least one of the first connection member and second connection member may include a self-healing membrane in the respective fluid channel and with the first connection member mated with the second connection member, the self-healing membrane forms a fluid-tight seal. The connection apparatus may include an indicator of the locked state between the first connection member and the second connection member. The indicator may be a visual indicator. In one aspect, the first and second connection members may each include a flat portion and a rounded portion, with the visual indicator formed by alignment of the flat portion of the first connection member with the flat portion of the second connection member and the alignment of the round portion of the first connection member with the round portion of the second connection member. In other aspects, the indicator may be a tactile indicator, such as the interaction of the at least one protrusion with a notch providing tactile indication of the locked state.

The first end of the second connection member may include sidewalls enclosing a hollow portion, where the sidewalls extend axially away from the second end of the second connection member, the sidewalls include the at least one protrusion, and the at least one protrusion extends inward. One of the first connection member and second connection member may be provided on a syringe adapter with the other connection member provided on at least one of a vial adapter and a patient connector. The shoulder may be rounded and the first portion of the at least one channel may define a non-linear path.

In another aspect, a connection apparatus for a medical device includes a first connection member having a first end and a second end, with the first connection member defining at least one channel adjacent the first end. The at least one channel having a first portion extending from a position adjacent the first end of the first connection member toward the second end of the first connection member. The at least one channel having a shoulder adjacent to the first end of the first connection member that defines a channel entry and a second portion extending from the first portion. The connection apparatus also includes a second connection member having a first end and a second end with the second connection member having at least one protrusion adjacent the first end. The at least one protrusion of the second connection member is configured to be received by the at least one channel of the first connection member. The first connection member and the second connection member have a locked state where the first connection member is secured to the second connection member. The at least one protrusion of the second connection member is positioned in the second portion of the at least one channel of the first connection member when the first and second connection members are in the locked state. The channel entry is wider than the first portion of the at least one channel of the first connection member.

The first portion of the at least one channel of the first connection member may be non-linear. The second portion of the at least one channel of the first connection member may extend in a transverse direction relative to a longitudinal axis of the first connection member. The second portion of the at least one channel may include a notch extending in an axial direction.

BRIEF DESCRIPTION OF THE DRAWINGS

FIG. 2 is a front view of the patient connector of FIG. 1 according to one aspect of the present invention.

FIG. 3 is a side view of the patient connector of FIG. 1 according to one aspect of the present invention.

FIG. 4 is a bottom perspective view of the patient connector of FIG. 1 according to one aspect of the present invention.

FIG. 5 is a top perspective view of the patient connector of FIG. 1 according to one aspect of the present invention.

FIG. 6 is a cross-sectional view of the patient connector of FIG. 1 according to one aspect of the present invention.

FIG. 7A is a front view of a connection member of the patient connector of FIG. 1 according to a further aspect of the present invention.

FIG. 13 is a front view of the vial adapter of FIG. 1 according to one aspect of the present invention.

FIG. 14 is a side view of the vial adapter of FIG. 1 according to one aspect of the present invention.

FIG. 17 is a cross-sectional view of the vial adapter of FIG. 1 according to one aspect of the present invention.

FIG. 18 is a perspective view of the syringe adapter and the patient connector of FIG. 1 in the process of being connected according to one aspect of the present invention.

FIG. 26A is a partial front cutaway view of an alternative aspect of a protrusion of a second connection member.

FIG. 26B is a partial front cutaway view of an alternative aspect of a protrusion of a second connection member.

FIG. 26C is a partial front cutaway view of an alternative aspect of a protrusion of a second connection member.

FIG. 26D is a partial front cutaway view of an alternative aspect of a protrusion of a second connection member.

FIG. 26E is a partial front cutaway view of an alternative aspect of a protrusion of a second connection member.

DESCRIPTION OF THE INVENTION

Figure 1:
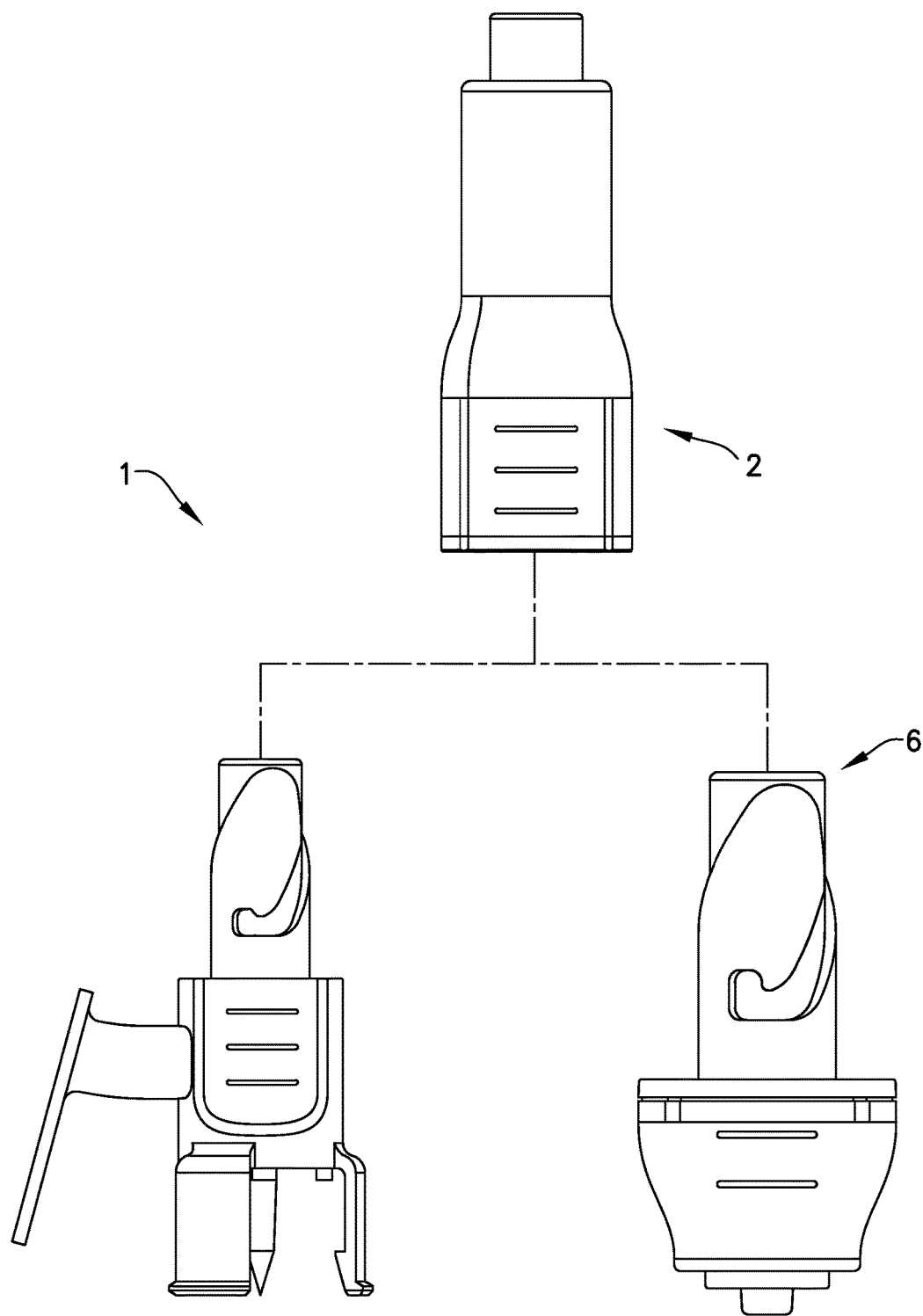
FIG. 1 is an exploded view of a system for the closed transfer of fluids according to one aspect of the present invention, showing a syringe adapter, a vial adapter, and a patient connector.
Figure 8:
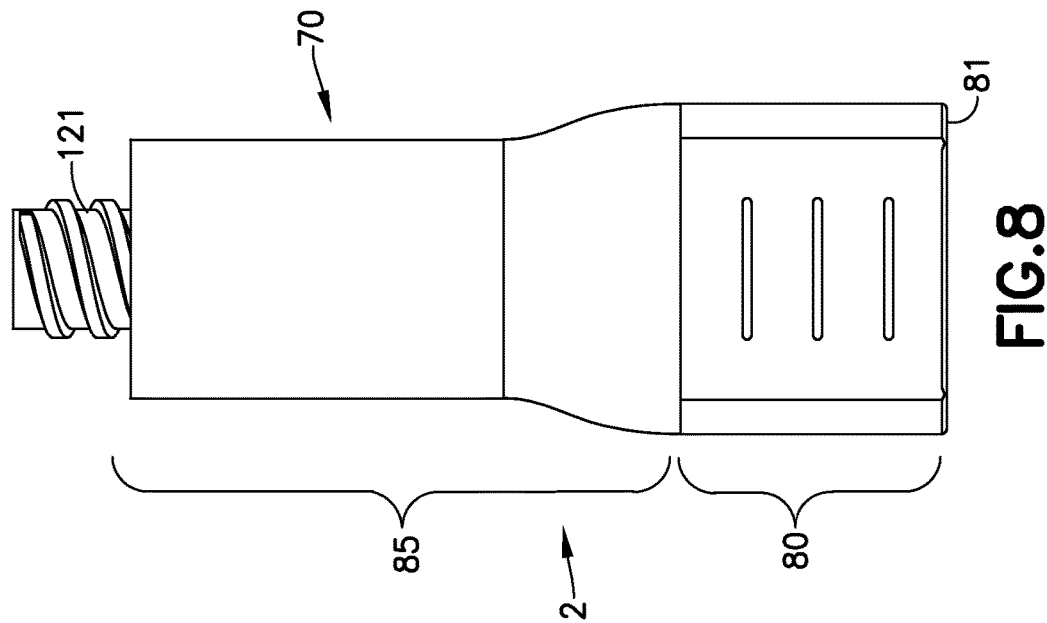
FIG. 8 is a front view of the syringe adapter of FIG. 1 according to one aspect of the present invention.

For purposes of the description hereinafter, the words "upper", "lower", "right", "left", "vertical", "horizontal", "top", "bottom", "lateral", "longitudinal", and like spatial terms, if used, shall relate to the described aspects as oriented in the drawing figures. However, it is to be understood that many alternative variations and aspects may be assumed except where expressly specified to the contrary. It is also to be understood that the specific devices and aspects illustrated in the accompanying drawings and described herein are simply exemplary aspects of the invention.

Referring to FIG. 1, one non-limiting aspect of system 1 for the closed transfer of fluids between a first container and a second container (not shown) includes a syringe adapter 2, a vial adapter 4, and a patient connector 6. The vial adapter 4 and the patient connector 6 include a first connection member 10 and the syringe adapter 2 includes a second connection member 70. Although FIG. 1 shows the first connection member 10 provided with the vial adapter 4 and the patient connector 6 and the second connection member 70 provided with the syringe adapter 2, those of skill in the art will understand and appreciate that the first connection member 10 and the second connection member 70 may independently be associated with any medical device. Further, the first connection member 10 may be associated with the syringe adapter 2 and the second connection member 70 may be associated with the vial adapter 4 and patient connector 6. Further, although not shown, the first connection member 10 may also be provided on an IV bag adapter or any other device typically utilized in CSTD systems. Thus the aspects illustrated in the accompanying figures should be considered merely, exemplary, non-limiting aspects.

Referring to FIGS. 1-7B and 13-17, the first connection member 10 according to one non-limiting aspect of the present invention includes a first end 20 and a second end 25. The first end 20 may be a solid structure, and the second end 25 may be any type of structure, for example and without limitation the second end 25 may be a gripping surface, an adapter for use with a CSTD, a visual indicator for determining proper engagement of the connection member with another connection member or other portion of the CSTD, or any useful combination thereof. First connection member 10 may be formed of any suitable material, such as, without limitation, plastics and medical-grade polymers. Such polymers are available from DuPont under the trade names Crastin®, Delrin®, Hytrel®, and Zytel®. In non-limiting aspects in which second end 25 is a specific type of adapter, first connection member 10 may be formed of multiple suitable materials, with first end 20 formed of a plastic or medical-grade polymer, or any suitable material.

With further reference to FIGS. 1-7B and 13-17, in a non-limiting aspect of the present invention, the first connection member 10 defines at least one channel 30 that extends from a portion of the first end 20 distal from the second end 25 to a portion of the first end 20 proximal the second end 25. The channel 30 is utilized in the process of mating the first connection member 10 and the second connection member 70 (shown in FIGS. 8-12), and may follow any useful path. In non-limiting aspects, the channel 30 follows a non-linear path, such as a substantially curved path as illustrated in FIGS. 1-7B and 13-17, although the channel 30 may also have a linear path or a path formed by a plurality of linear portion.

The channel 30 may have several discrete portions, including a channel entry 50, an axial or substantially axial portion 35 extending along the length of the first end 20 of first connection member 10, and a transverse portion 60 proximal to the second end 25 that extends transversely relative to the axial portion 35. First end 20 of first connection member 10, which includes channel entry 50, further includes a shoulder 40 defining the channel entry 50. In non-limiting aspects, shoulder 40 is rounded such that objects that contact the shoulder 40 are guided into the channel entry 50. The rounded nature of the shoulder 40 also permits mating of the first connection member 10 with the second connection member 70 (FIGS. 8-12) without the need for the members to be in any predetermined orientation, increasing the ease of achieving secure connections. Rather than providing a rounded shoulder 40, the shoulder 40 may also come to a pointed peak or have any other suitable shape to guide the second connection member 70 into the channel entry 50 regardless of the orientation of the mating components relative to each other.

In non-limiting aspects, the transverse portion 60 of channel 30 is substantially perpendicular to the axial portion 35 of channel 30. In non-limiting aspects, the channel entry 50 is advantageously wider than the remaining portions 35, 60 of the channel 30, to increase ease of mating first connection member 10 with second connection member 70, which will be described. In non-limiting aspects, the channel 30 includes at a terminus of the transverse portion 60 at least one notch 100. In certain non-limiting aspects, the notch 100 extends axially, either distally away from the second end 25 of the first connection member 10 or proximally, towards the second end 25 of the first connection member 10.

In non-limiting aspects as illustrated in FIG. 7A, at the terminus of transverse portion 60 of channel 30, a plurality of notches is provided. In non-limiting aspects, a notch 110 extends distally away from second end of the connection member and a notch 120 extends proximally towards the second end of the connection member. In such a configuration, a greater number of arrangements for securing protrusion 90 of a second connection member, and thus for securing first connection member and second connection member in a mated configuration, are possible. Those of skill in the art will understand and appreciate the wide variety of mechanisms, such as springs and other compliant and elastic devices and apparatuses, which are useful for maintaining protrusion 90 within notches 110, and/or 120. The notches 110, 120 define bumps or structure that may provide a tactile and auditory indication that the device is in a locked state. The protrusion 90 may only be maintained in the locked position through the engagement of the protrusion 90 with the structure that defines the notches 110, 120 and may not be utilized in connection with a biasing member. In particular, the protrusion 90 and notches 110, 120 may be configured to maintain a locked position within the transverse portion 60 until a sufficient torque is applied to push the protrusion 90 past the notches 110, 120.

Figure 7B:
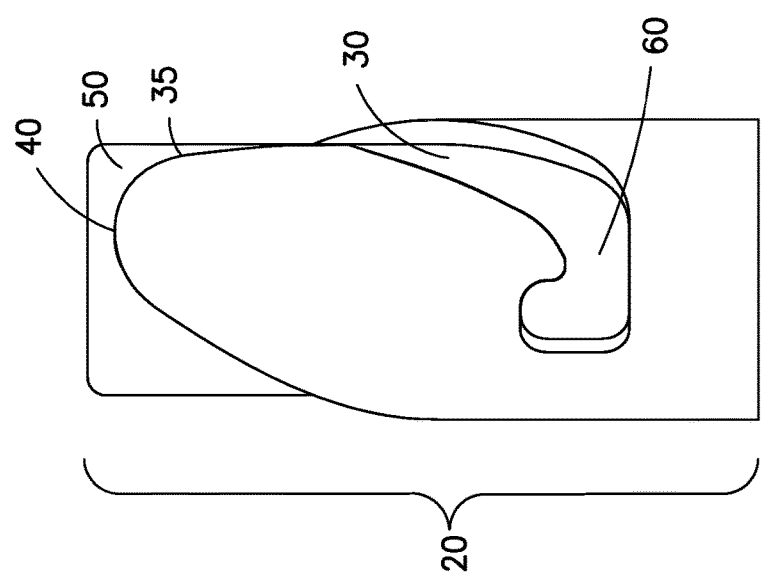
FIG. 7B is a front view of a connection member of the patient connector of FIG. 1 according to another aspect of the present invention.
Figure 10:
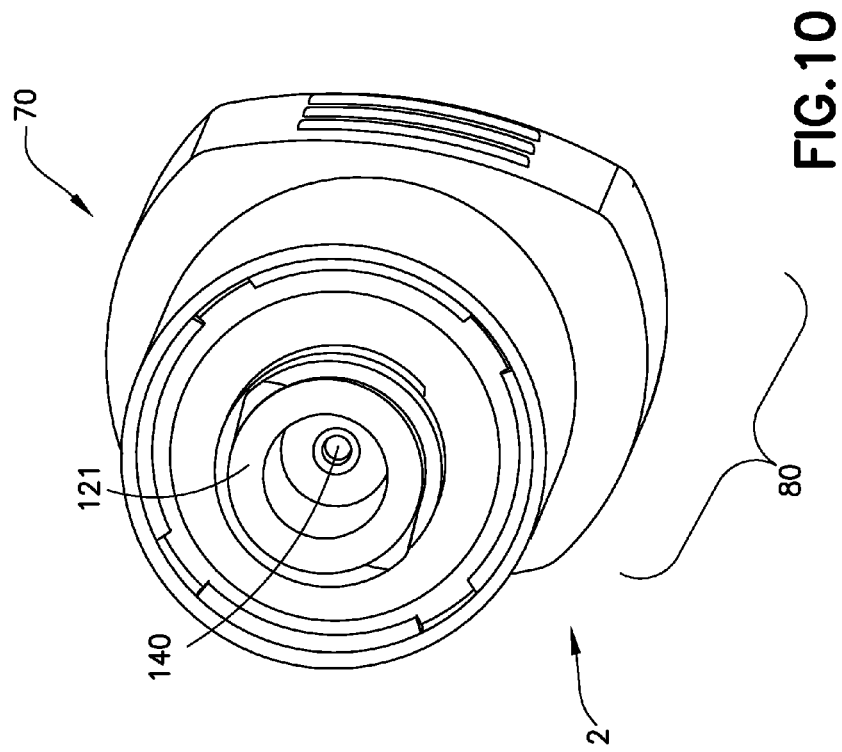
FIG. 10 is a top perspective view of the syringe adapter of FIG. 1 according to one aspect of the present invention.
Figure 9:
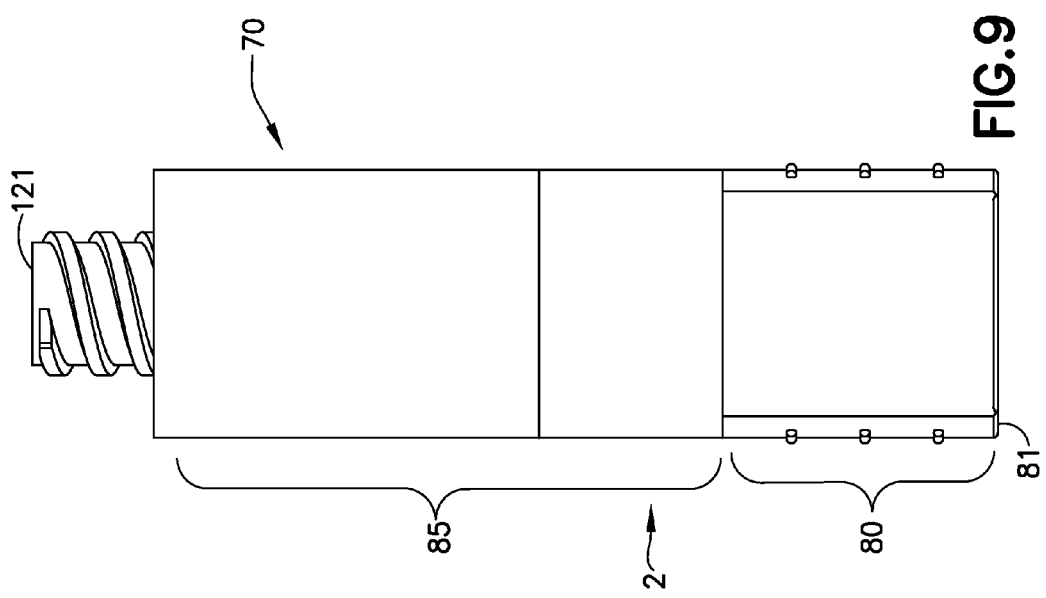
FIG. 9 is a side view of the syringe adapter of FIG. 1 according to one aspect of the present invention.

In non-limiting aspects as illustrated in FIG. 7B, at the terminus of transverse portion 60 of channel 30, a single notch is provided. In non-limiting aspects, a notch 110 extends distally away from second end of the connection member. As noted above, the notch 110 may form a bump and provide a tactile and auditory indication that the device is in a locked state. The protrusion 90 may only be maintained in the locked position through the engagement of the protrusion 90 with the structure that defines the notch 110 and may not be utilized in connection with a biasing member. In particular, the protrusion 90 and notch 110 may be configured to maintain a locked position within the transverse portion 60 until a sufficient torque is applied to push the protrusion 90 past the notch 110.

With reference to FIGS. 2-6, the first connection member 10 is shown in connection with the patient connector 6. The patient connector 6 defines a fluid channel 130 that extends through the patient connector 6. Second end 25 further includes surface 26 that allows for fitted mating with second connection member 70. Said surface 26 may be flat or any other configuration that allows for close mating of first and second connection members 10, 70. Surface 26 of first connection member 10 may also include elastic or compliant means so that first 10 and second 70 connection members can be urged together during mating and unmating. The patient connector 6 also includes a male or female threaded luer lock 122 for connecting the patient connector 6 to a fluid conduit that is in fluid connection with a patient's circulation, such as an intravenous patient line.

With reference to FIG. 6, the fluid channel 130 passes through the patient connector 6 and the first connection member 10 and is configured to be in fluid communication with a corresponding fluid channel of a second connection member 70 such that when the first and second connection members 10, 70 are mated, a fluid path is formed therethrough. Fluid channel 130 and/or first end 20 and second end 25 of first connection member 10 may include seals or membranes in any advantageous location to aid in the formation of a fluid-tight seal when first connection member 10 is mated to second connection member 70. Such seals and membranes are known to those of skill in the art, and may include self-healing seals and membranes and should be selected based on the intended use for the device such as biocompatibility, chemically inert, and compatible with any chemical reagents or treatments contained therein, be FDA and/or OSHA approved, and suitable for use in CSTDs. Such seals may be formed out of natural materials such as rubber, synthetic polymers, and/or silicone, such as room temperature vulcanizing silicone. In particular, the proximal end of the first end 20 of the connector may include a membrane that mates a forms a seal with a corresponding member of the second connection member 70.

Referring to FIGS. 8-12, the syringe adapter 2 includes the second connection member 70, which is configured to mate with first connection member 10. Second connection member 70 includes first end 80 and second end 85. Second connection member 70 may be formed out of any suitable material. For example, and without limitation, second connection member 70 may be formed out of plastic or a medical-grade polymer. In non-limiting aspects, second connection member 70 is formed from the same material as first connection member 10 or first end 20 of first connection member 10. First end 80 further includes surface 81 that allows for fitted mating with surface 26 of first connection member 10. Said surface 81 may be flat or any other configuration that allows for closed mating of first and second connection members 10, 70 through interaction of surfaces 26 and 81. Surface 81 of second connection member 70 may also include elastic or compliant structure so that first 10 and second 70 connection members can be urged together during mating and unmating. In non-limiting aspects, second connection member 70 may include a male or female threaded luer lock 121.

Figure 12:
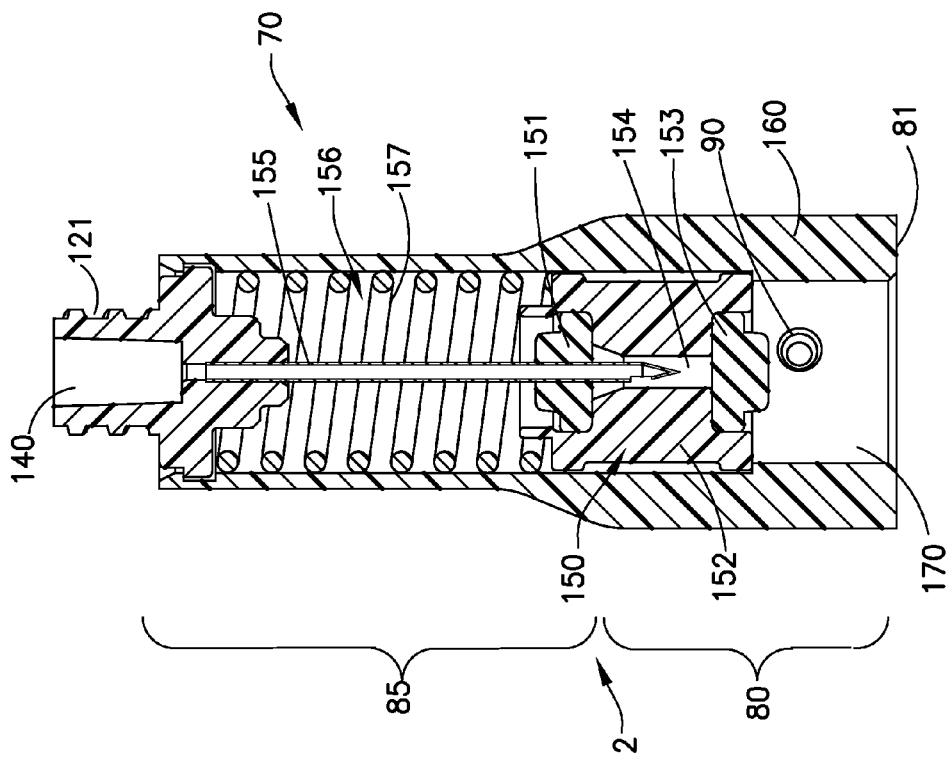
FIG. 12 is a cross-sectional view of the connection member of the syringe adapter of FIG. 1 according to one aspect of the present invention.
Figure 11:
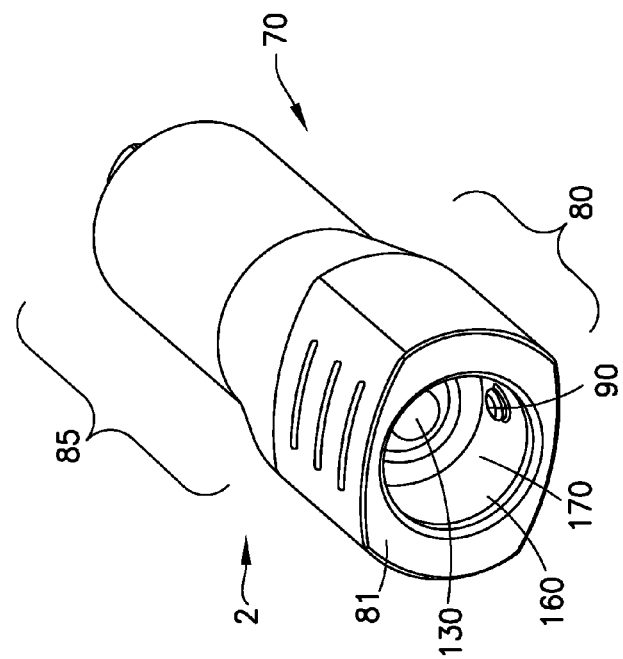
FIG. 11 is a bottom perspective view of the syringe adapter of FIG. 1 according to one aspect of the present invention.
Figure 16:
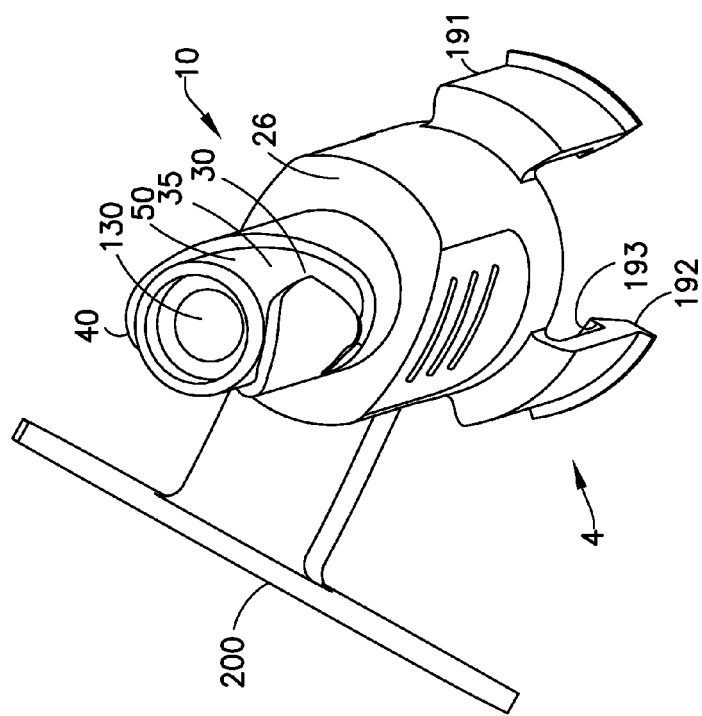
FIG. 16 is a top perspective view of the vial adapter of FIG. 1 according to one aspect of the present invention.
Figure 15:
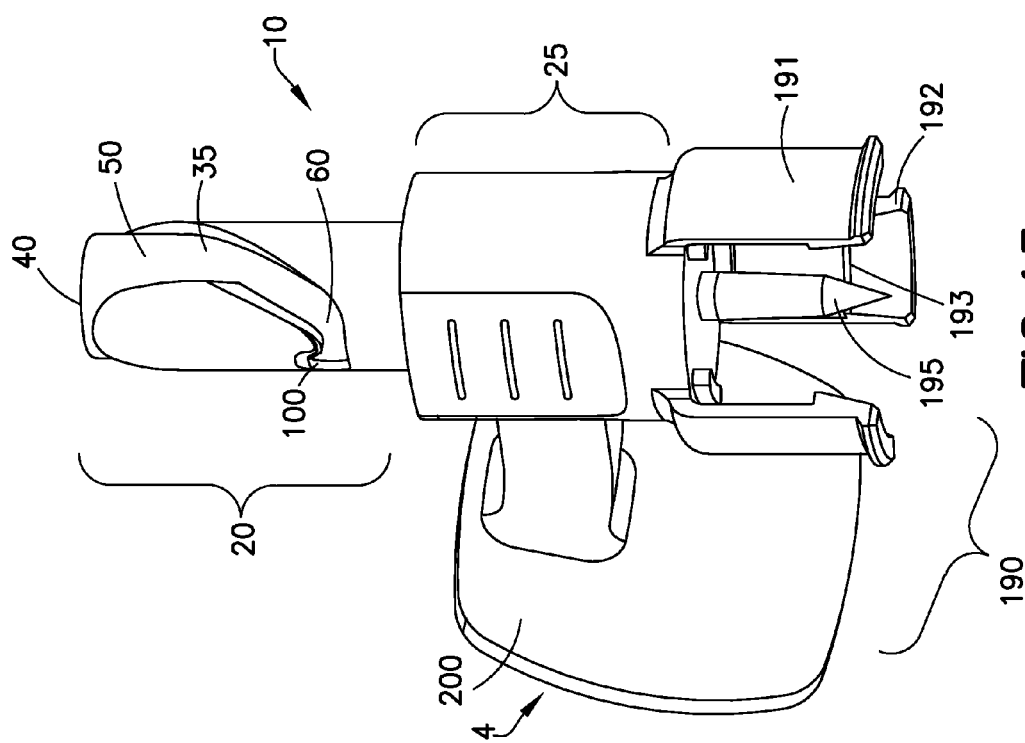
FIG. 15 is a bottom perspective view of the vial adapter of FIG. 1 according to one aspect of the present invention.

Referring to FIG. 12, syringe adapter 2 defines fluid channel 140 that passes through first end 80 and second end 85. The syringe adapter 2 allows for connection (through luer lock 121) to a syringe to, for example and without limitation, reconstitute a drug, or aspirate a drug from a vial (through interaction with a vial adapter having a connection member). Although a luer lock 121 is shown, any other suitable connection may be utilized. Aspirated drugs can be provided to a patient through interaction with the patient connector 6 having the first connection member 10. First end 80 of the second connection member 70 has sidewalls 160 that define an interior cavity 170 including at least one protrusion 90. Protrusion 90 is dimensioned to interact with channel 30 of first connection member 10. Specifically, in a non-limiting aspect, when first connection member 10 is mated with second connection member 70 by engaging first end 20 of first connection member 10 with first end 80 of second connection member 70, first end 20 of first connection member 10 engages the first end 80 of second connection member 70.

Referencing FIGS. 2-5 and 11, if protrusion 90 is aligned with channel entry 50, second connection member 70 will engage with first connection member 10. However, if protrusion 90 is not aligned with channel entry 50, protrusion 90 may contact shoulder 40. In certain aspects, where shoulder 40 is advantageously rounded or sloped, protrusion 90 is guided into channel entry 50 by the shape of the shoulder, allowing for mating of first connection member 10 and second connection member 70. The rounded nature of the shoulder 40 permits mating of the first connection member 10 with a second connection member 70 without the need for the members to be in any predetermined orientation, increasing the ease of achieving secure connections. Those of skill in the art will understand that the above-described principle, and mating process, will likewise function if first connection member 10 has a protrusion extending radially outward and second connection member 70 has a channel on an interior surface. Thus, the illustrations in the accompanying drawings and described herein should be considered exemplary aspects of the invention.

With continuing reference to FIGS. 2-5 and 11, when protrusion 90 is aligned with channel entry 50, protrusion 90 can enter channel 30 and allow for engagement of first connection member 10 and second connection member 70. As first connection member 10 and second connection member 70 come into further engagement, protrusion 90 proceeds further along channel 30, proceeding through axial portion 35. In non-limiting aspects in which channel 30 is non-linear, passage of protrusion 90 along a path that may be, for example and without limitation, curved, rotates one or both of the connection members 10, 70 relative to the other connection member, or relative to each other.

The non-linear, or curved, path of the channel 30 brings protrusion 90 to the transverse portion 60 of the path 30 with rotation of the first and/or second connection members 10, 70. Continued rotation of the first connection member 10 and/or second connection member 70 moves protrusion 90 along transverse portion 60 of path 30, and protrusion 90 approaches notch 100. As first connection member 10 and/or second connection member 70 rotate further, protrusion 90 reaches the terminus of the path 30, and further rotation is not possible. Release of first connection member 10 and/or second connection member 70 allows protrusion 90 to enter notch 100. This entry prevents disengagement of the mated first connection member 10 and second connection member 70. Protrusion 90 remains engaged with notch 100 through any suitable arrangement, for example and without limitation through use of compliant structure such as, for example and without limitation, compression coil/helical springs and tension coil/helical springs. Those of skill in the art are aware of the types of devices that can provide sufficient force or tension to maintain protrusion 90 in notch 100, and thus maintain engagement of the connection members. As noted in connection with the aspects shown in FIGS. 7A and 7B, the notches 110, 120 define bumps or structure that create an interference fit between the protrusion 90 and the first connection member 10 such that, once the protrusion 90 is forced past the bump or bumps, the first connection member 10 will remain connected to the second connection member 70 unless a predetermined amount of torque is applied to the member 10, 70 to force the protrusion 90 past the bump(s) again and back through the path 30. Accordingly, the protrusion 90 of the second connection member 70 has a clearance fit when moving into notch 100 of the first connection member 10 shown in FIG. 2 and require a biasing force to maintain the protrusion 90 within the notch 100 whereas the notches 110, 120 of the first connection member 10 shown in FIGS. 7A and 7B may define a friction engagement with the protrusion 90 such that the biasing force is unnecessary to maintain the locked engagement. However, the notch 100 shown in FIG. 2 and the notches 110, 120 of FIGS. 7A and 7B may each be utilized in a clearance or friction fit engagement with the protrusion 90 and with or without a biasing force to maintain a secure connection.

In certain non-limiting aspects, first end 20 of first connection member 10 is a solid cylinder and first end 80 of second connection member 70 defines a hollow cylindrical body with the protrusion 90 facing inward into the hollow portion. Mating of the two connection members 10, 70 is accomplished by inserting first end 20 of first connection member 10 into the hollow body of first end 80 of second connection member 70 or, alternatively, sliding the hollow body of first end 80 of second connection member 70 over first end 20 of first connection member 10. Those of skill in the art will appreciate that in additional aspects within the scope of the present invention, the protrusion may be present on first connection member 10 and face outward, with second connection member 70 having a channel for receiving said protrusion and a notch for forming a positive lock with said protrusion.

Referring again to FIG. 12, the second connection member 70 includes a seal or membrane apparatus 150. Seal or membrane apparatus 150 is configured to mate with a corresponding seal on the second connection member 10 to form a sealed interface between the first and second connection members 10, 70 during the transfer of fluids. Seal or membrane apparatus 150 may also be a part of first connection member 10.

In non-limiting aspects, seal or membrane apparatus 150 may be self-healing and may also be a multi-component seal or membrane. For example, in the aspect illustrated in FIG. 12, seal apparatus 150 includes a first seal 151, a seal carrier 152, and a second membrane 153. The seal carrier 152 receives the first seal 151 at one end and the second seal 153 at the opposite end. The first and second seals 151, 153 define a space 154 therebetween. The second connection member also includes a needle 155 in fluid communication with the fluid channel 140 and a biasing member 157, such as a spring, positioned between the luer lock 121 and the seal apparatus 150. The seal apparatus 150 is configured to move within the housing between a shielded and unshielded position. As discussed below, when the second connection member 70 is mated with the first connection member 10, the seal apparatus 150 is moved upwardly within the second connection member 70 thereby storing energy within the biasing member 157, i.e., compressing the biasing member. When the seal apparatus 150 is moved within the second connection member 70, the needle 155 pierces the seal 153 and places the first connection member 10 in fluid communication with the second connection member 70 to transfer fluid between a first container, such as a syringe, and a second container, such as a vial, IV bag, or patient IV line. During connection of the second connection member 70 with the first connection member 10, the seal 153 may engage and form a sealed member with a corresponding seal member provided on the first connection member to prevent the leakage of any fluid during the transfer of fluid through the first and second connection members 10, 70. In an unconnected state of the second connection member 70, the distal tip of the needle 155 is positioned in the space 154 between the first and second seals 151, 153 to contain the distal tip of the needle 155 within the carrier 152. Alternative arrangements for the seal or membrane apparatus 150 may be utilized in connection with the first and second connection members 10, 70.

Seals or membranes suitable for use with the present invention in the aspect shown in FIG. 12 and described above, or with a singular self-healing seal or membrane, are well-known to those in the art and allow penetration by a point, i.e., needle, such that upon withdrawal of the point, the seal substantially reseals to preclude fluid passage. Suitable materials for the seals are well known in the art and should be selected based on the intended use for the device such as biocompatibility, chemically inert, and compatible with any chemical reagents or treatments contained therein, be FDA and/or OSHA approved, and suitable for use in CSTDs. Such seals may be formed out of natural materials such as rubber, synthetic polymers, and/or silicone, such as room temperature vulcanizing silicone.

In any aspect of the present invention, additional fluid-tight seals or membranes may be provided at any advantageous location to increase safety for the user. For example, and without limitation, materials suitable for forming fluid-tight seals may also be provided on the surface 26 of second end 25 of first connection member 10 that contacts surface 81 of first end 80 of second connection member 70 and/or on the surface 81 of the first end 80 of the second connection member 70 that contacts surface 26 the second end 25 of the first connection member 10. As noted above, the proximal end of the first end 30 of the first connection member 10 may be provided with a seal that is configured to engage the seal 153 of the second connection member 70 such that when the first connection member 10 and the second connection member 70 are mated, a fluid-tight seal is formed therebetween and any possible leakage from an accident can be contained in the fluid path formed by fluid channels 130 and 140.

The interaction of the protrusion 90 of the second connection member 70 with the channel 30 and, ultimately, the notch 100, 110, and/or 120 of the first connection member 10 forms a positive lock, and secures the first connection member 10 with the second connection member 70. Because protrusion 90 remains engaged with notch 100 through any suitable means, for example and without limitation through use of biasing member 157 (referencing FIG. 12) such as, for example, and without limitation, compression coil/helical springs and tension coil/helical springs, an additional force apart from mere rotation is required to break the positive lock. The additional force required to break the positive lock may be urging the first connection member 10 and/or second connection member 70 towards each other, or pulling the same away from each other. Accordingly, in one aspect, the force of the biasing member 157 must be overcome to disconnect the first connection member 10 from the second connection member 70. In other words, the biasing force of the biasing member 157 maintains the first and second connection member 10, 70 in a locked, connected position by biasing the protrusion 90 within the notch 100. When the force of the biasing member 157 is overcome, the second connection member 70 may be rotated and removed from the first connection member 10. As noted above, when the first connection member 10 is disconnected from the second connection member 70, the biasing member 157 transitions the seal carrier 152 back to the position shown in FIG. 12 with the distal end of the needle 155 positioned within the space 154. With respect to the aspects shown in FIGS. 7A and 7B, the bump(s) defined by the notches 110, 120 create an interference fit between the protrusion 90 and the first connection member 10 such that, once the protrusion 90 is forced past the bump or bumps, the first connection member 10 will remain connected to the second connection member 70 unless a predetermined amount of torque is applied to the members 10, 70 to force the protrusion 90 past the bump(s) again and back through the path 30. Accordingly, in connection with the aspects of FIGS. 7A and 7B, the biasing member 157 is not necessarily needed to create a positive lock between the members 10, 70 such that the members do not need to be axially moved relative to each other to overcome the positive lock.

Turning to FIGS. 13-17, as indicated elsewhere, connection members 10 and 70 can be utilized in connection with any suitable medical device and in particular, CSTDs. In certain non-limiting aspects, the connection apparatus may be utilized with structures or devices for use in CSTD systems, such as the patient connector 6 shown in FIGS. 2-6 and the syringe adapter 2 shown in FIGS. 8-12. The connection apparatus may also be provided in connection with vial adapters (as shown in FIGS. 13-17), for forming a connection with a vial containing, for example and without limitation, a lyophilized compound. The vial adapter 4 may allow for formation of a fluid and air-tight seal to prevent exposure to the compound, which may be toxic. The additional structures may also include syringe adapters, to allow for reconstitution of compounds and transfer of reconstituted compound, and/or patient connectors, to allow for introduction of the compound to the patient's circulatory system by way of an intravenous access.

With reference to FIG. 13, a non-limiting aspect of the first connection member 10 of the connection apparatus is provided in connection with the vial adapter 4. First connection member 10 includes first end 20 and second end 25. First end 20 includes a guide channel 30 having an axial portion 35 and a transverse portion 60. Transverse portion 60 of channel 30 has a terminus at which a notch 100 is located. Those of skill will appreciate that any type of notch, for example those denoted 110 and/or 120 in FIGS. 7A and 7B may be utilized within the scope of this invention. Channel 30 further includes channel opening 50 defined at least in part by shoulder 40, which may be rounded in non-limiting aspects. Second end 25 of first connection member 10 may further include a vial attachment 190. This vial attachment allows for connection to a vial containing a lyophilized compound, though compounds in a liquid state may also be in such a vial when the liquid compound requires safe and secure transfer to a syringe and/or a patient.

In further non-limiting aspects, the vial adapter 4 may include further structures or features that add additional safety and security to the reconstitution and/or withdrawal of a compound from a vial. For example, and without limitation, the vial attachment 190 may include arms 191 for attachment to a vial (not shown). Arms 191 may include protrusions 192 that are angled to allow for ease of attachment to a vial. For example, in the aspect shown in FIGS. 13-17, angled portions 192 of arms 191 allow for a vial to be attached to vial attachment 190 by forcing vial into space between arms 191, or by forcing vial attachment 190 onto a vial such that the arms 191 encircle the neck of the vial. In certain non-limiting aspects, surfaces 193 can engage with a vial and lock the vial into place, preventing accidental separation of vial and vial attachment 190. In non-limiting aspects, upon mating of the vial with the vial attachment 190, spike 195 pierces the vial. Although not shown, a seal or membrane may be positioned at the proximal end of the first end 20 of the first connector 10 such that it is configured to mate with the seal 153 of the syringe adapter 2.

In further non-limiting aspects, and as shown in FIGS. 13-17, the vial adapter 4 may further include a pressure equalization member 200. The pressure equalization member 200 is shown schematically and may be a balloon-type arrangement, bellows-type arrangement, or any other type of pressure equalization device known to those of skill in the art. Such pressure equalization members reduce the likelihood of exposure by reducing the risk of release of toxic or harmful substances through alteration or differences in pressures between the syringe and vial, or between vial and atmosphere by maintaining a neutral pressure during injection into or aspiration from a vial, thus reducing the risk of sprayback.

With reference to FIG. 17, the vial adapter 4 defines a fluid channel 130 that is configured to be in fluid communication with the interior of a vial (not shown). The vial adapter 4 further defines a vent channel 131 to allow for communication between a vial and the pressure equalization member 200. The vent channel 131 allows the pressure equalization member 200 to equalize the pressure within the vial during mating, reconstitution, and aspiration, and reduces the risk of sprayback.

With reference to FIGS. 1-6 and 8-19, in certain non-limiting aspects, the system 1 includes one or more indicators that provide an indication that the first connection member 10 and second connection member 70 are in a locked state, i.e., that the protrusion 90 and notch 100, 110, and/or 120 have formed a positive lock. The indicator may be any type of useful indicator, for example it may provide indication of a locked state by visual, tactile, or auditory means, or by any combination of such means. For example, and without limitation, the movement of the protrusion 90 into notch 100, 110, and/or 120 may provide an auditory and/or tactile indication of the formation of a positive lock, by, for example, a click or other familiar noise, and/or movement of the protrusion 90 into a positive lock with notch 100, 110, and/or 120.

In other non-limiting aspects, the indicator may be visual alone, or visual in connection with tactile or auditory. For example, and without limitation, a possible indicator is shown in the prior figures, but is specifically referenced in FIG. 19 and shows a visual indicator 165 that comprises the second end 25 of first connection member 10 and first end 80 of second connection member 70. The indicator 165 is such that when the first connection member 10 and second connection member 70 are in a locked stated because of interaction of protrusion 90 and notch 100, 110, and/or 120, and interaction of surface 26 of first connection member 10 and surface 81 of second connection member 70, the geometry of the exterior of second end 25 of first connection member 10 and the first end 80 of second connection member 70 form a visual indication of that locked state. The visual indication may be a formation of a particular geometry and/or alignment of one or more visual indicators present on the second end 25 of first connection member 10 and the first end 80 of second connection member 70.

Figure 19:
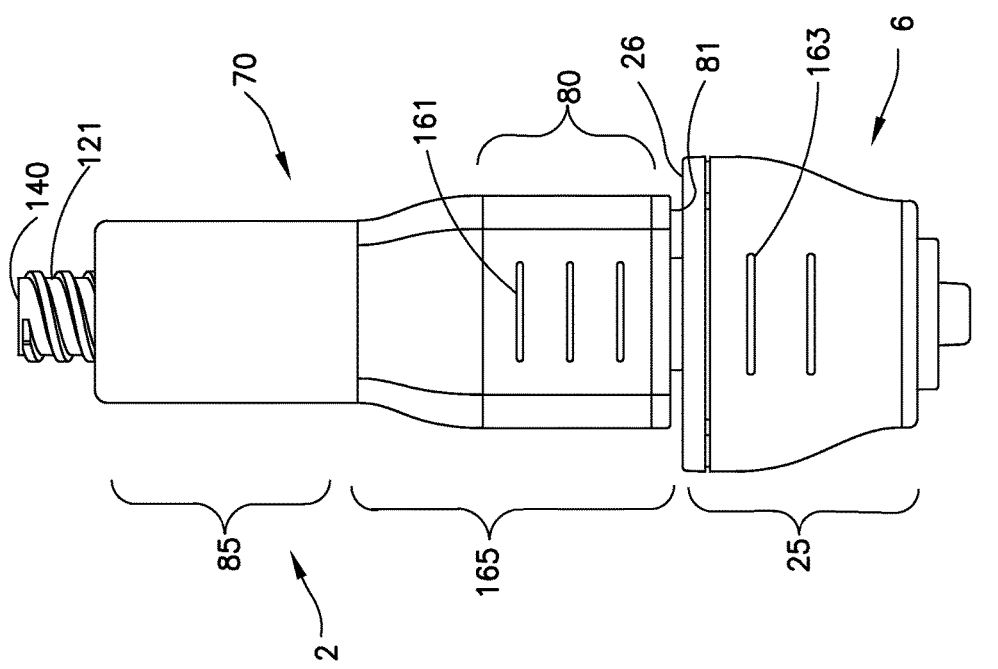
FIG. 19 is a perspective view of the syringe adapter and the patient connector of FIG. 1 in a connected state according to one aspect of the present invention.

For example and without limitation, and with continuing reference to FIG. 19, indicator 165 can include a general geometric shape formed by the second end 25 of first connection member 10 and the first end 80 of second connection member 70. The presence of a locked state between first connection member 10 and second connection member 70 is indicated by a uniform geometry of the visual indicator 165. In addition, visual indication may be provided by alignment of one or more visual indicators, such as ribs 161, 162, and 163 on first connection member 10 and second connection member 70. In addition to providing a visual indication of a locked state, ribs 161, 162, and 163 may also provide support for gripping the first connection member 10 and second connection member 70 for mating and unmating.

Figure 20:
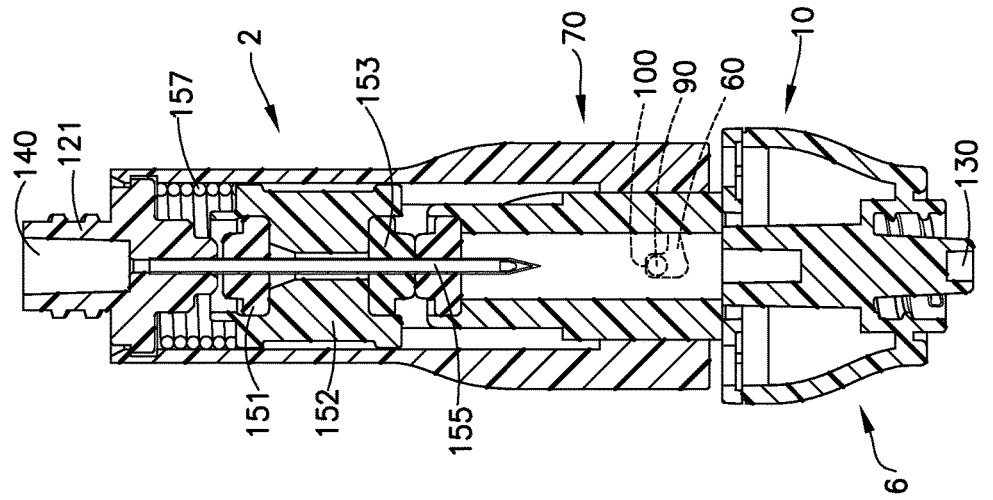
FIG. 20 is a cross-sectional view of the syringe adapter and the patient connector of FIG. 1 in a connected state according to one aspect of the present invention.

With reference to FIG. 20, the syringe adapter 2 is shown in a connected or mated state with the patient connector 6 according to one aspect of the present invention. Interaction of protrusion 90 with notch 100 is shown in dashed lines. This interaction results in a positive lock whereby mere rotation of either first 10 or second 70 connection members relative to the other is not sufficient to unmate the devices. Rather, application of some axial force (either pushing first 10 and second 70 connection members together or pulling them apart) is required to disengage protrusion 90 from notch 100. Additionally, interaction of first connection member 10 with second connection member 70 compresses the compliant member 157 within second connection member 70. This compression allows for needle 155 and fluid path 140 to become fluidly connected with fluid channel 130 of first connection member 10, and allows for passage of fluid between the syringe adapter 2 and patient connector 6 and consequently between first and second containers and/or an intravenous patient line.

Figure 21:
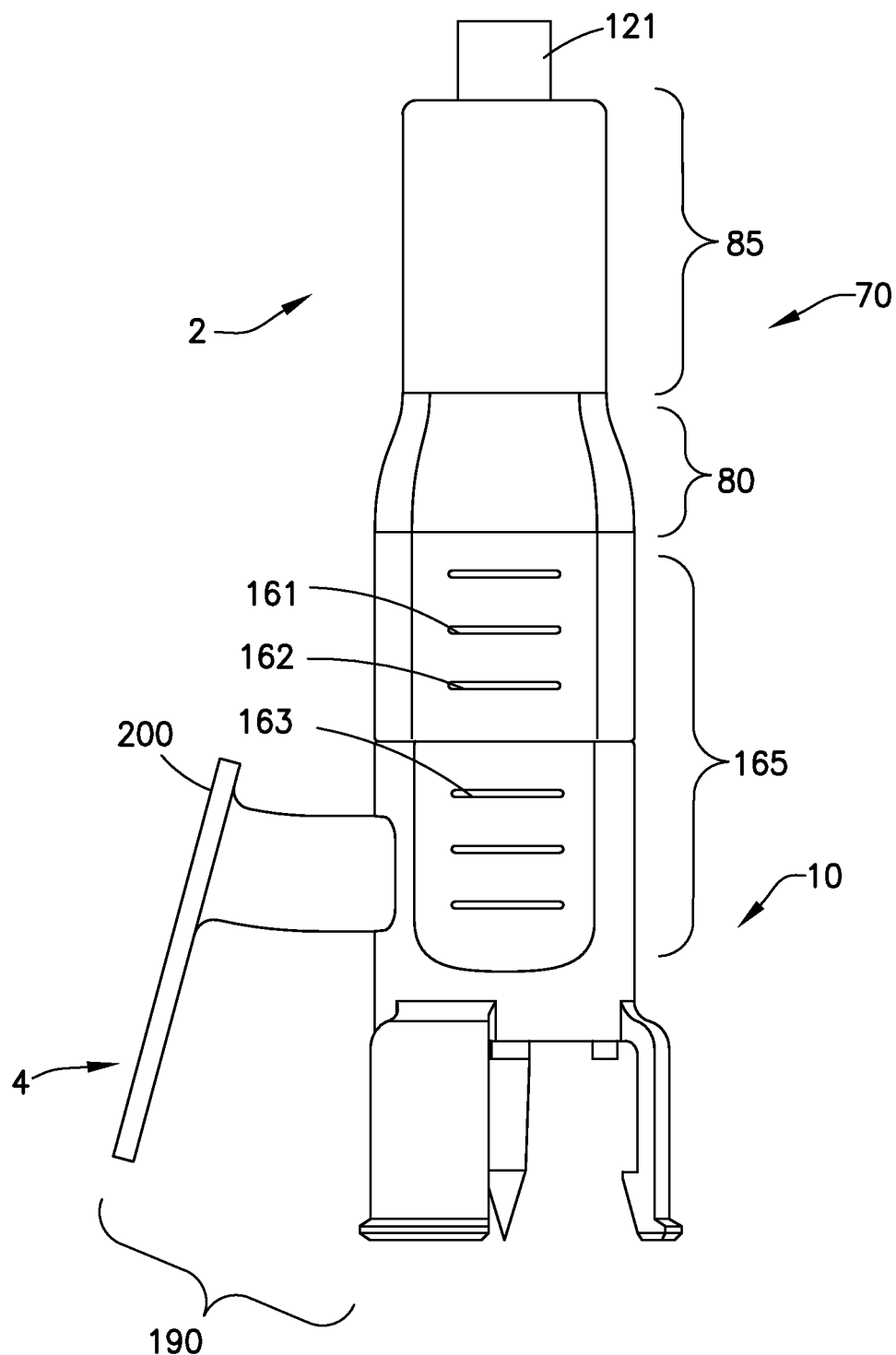
FIG. 21 is a front view of the syringe adapter and the vial adapter of FIG. 1 in a connected state according to one aspect of the present invention.

With reference to FIG. 21, the syringe adapter 2 is shown in a connected or mated state with the vial adapter 4 according to one aspect of the present invention. The syringe adapter 2 is mated to the vial adapter 4 to form a positive lock in the same manner described above with respect to the connection between the syringe adapter 2 and the patient connector 6. The syringe adapter 2 and the vial adapter 4 provide the same indicator 165 described above.

Also provided by one aspect of the present invention is a method of forming a connection for a medical device or connection apparatus. The method includes providing a first connection member 10 having a first end 20 and a second end 25. The first end 20 includes a channel 30 having a first, axial portion 35. The first end 20 may also include a shoulder 40 that at least partially defines a channel entry 50. The channel 30 of the first connection member 10 may be non-linear, and includes a transverse portion 60 that is transverse relative to the axial portion 35. The method further includes providing a second connection member 70 having a first end 80 and a second end 85. The first end 80 of the second connection member 70 further includes a protrusion 90, the protrusion configured to be received within the channel 30 of the first connection member 10. The method further includes mating the first connection member 10 with the second connection member 70, though those of skill will appreciate that the second connection member 70 can be mated with the first connection member 10 within the scope of the present invention.

In certain aspects, additional features of the first and second connection members 10, 70 may be included in the method of mating the connection members. For example and without limitation, the transverse portion 60 of the channel 30 may include at its terminus one or more notches 100, 110, and/or 120. In such an aspect, the mating step includes rotation of one or both of the connection members 10, 70 relative to one another as the protrusion 90 proceeds through channel 30. Further rotation brings protrusion 90 into engagement with one or more notches 100, 110, and/or 120 to form a locked state between connection members of the medical device or connection apparatus. Formation of a lock between connection members 10, 70 allows for fluid channel 130 in first connection member 10 and fluid channel 140 in second connection member 70 to form a fluid path through the medical device or connection apparatus.

Turning to FIGS. 22-25, a second aspect of system for the closed transfer of fluids is shown. The system includes a first connection member 2010 provided in connection with a vial adapter. The first connection member 2010 having a first end 2020 and a second end, which in the figures includes vial attachment 2190. The first end 2020 may be a solid structure, and the second end may be any type of structure, for example a vial attachment 2190. First connection member 2010 may be formed of any suitable material, such as, without limitation, plastics and medical-grade polymers. Such polymers are available from DuPont under the trade names Crastin®, Delrin®, Hytrel®, and Zytel®. In non-limiting aspects in which the second end is a specific type of adapter, first connection member 2010 may be formed of multiple suitable materials, with first end 2020 formed of a plastic or medical-grade polymer, or any suitable material.

With further reference to FIGS. 22-25, in a non-limiting aspect of the present invention, first connection member 2010 also includes at least one channel 2030 that extends from a portion of the first end 2020 distal from the second end to a portion of the first end 2020 proximal the second end. The channel 2030 is utilized in the process of mating the first connection member 2010 and a second connection member 2070, and may follow any useful path. In comparison to the non-limiting aspects shown in FIGS. 2-5, the aspect of the first connection member 2010 shown in FIGS. 22-25 includes a less curved, more axially linear channel.

The channel 2030 may have several discrete portions, including a channel entry 2050, an axial or substantially axial portion extending along the length of the first end 2020 of first connection member 2010, and a transverse portion 2060 proximal to the second end that extends transversely relative to the axial portion. First end 2020 of first connection member 2010, which includes channel entry 2050, further includes a shoulder 2040 defining the channel entry 2050. In non-limiting aspects, shoulder 2040 is not rounded, as shown in the aspect depicted in FIGS. 2-5. Rather, shoulder 2040 is more angular, but still defines, and guides a protrusion of a second connection member into, channel entry 2050. The shoulder 2040 permits mating of the first connection member 2010 with a second connection member 2070 without the need for the members to be in any predetermined orientation, increasing the ease of achieving secure connections. The channel 2030 may also define a notch 2100 to receive a portion of the second connection member 2070.

Figure 23:
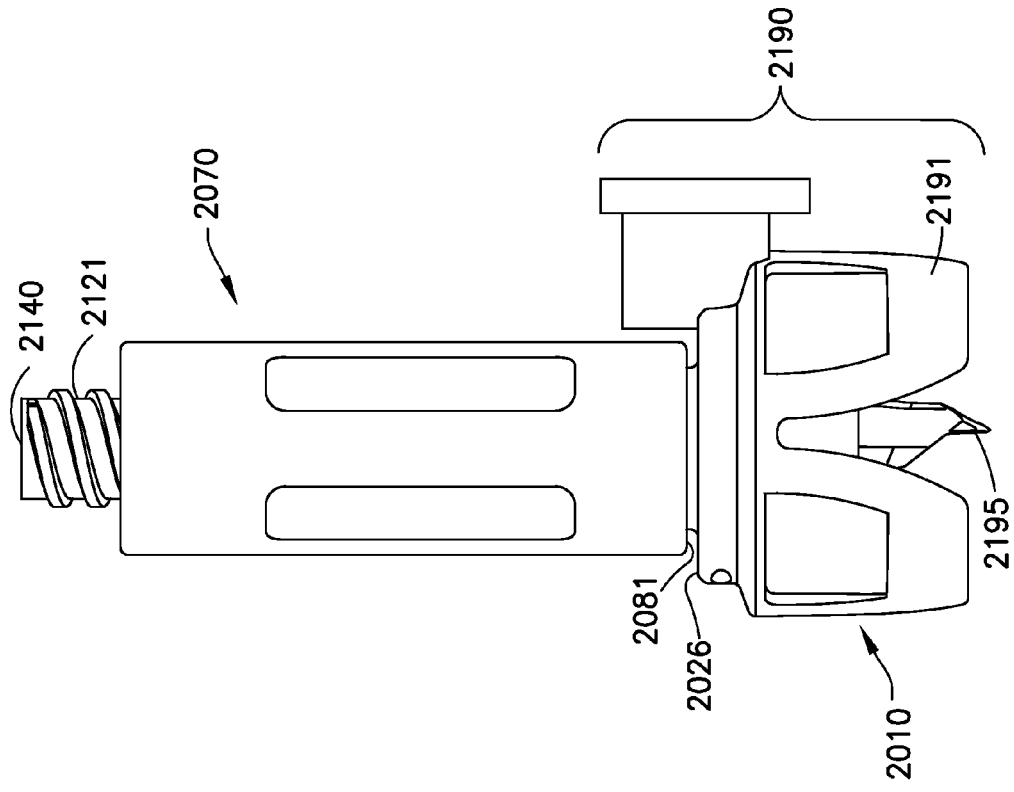
FIG. 23 is a front view of a syringe adapter according to a second aspect of the present invention, showing the syringe adapter connected to the vial adapter of FIG. 22.
Figure 22:
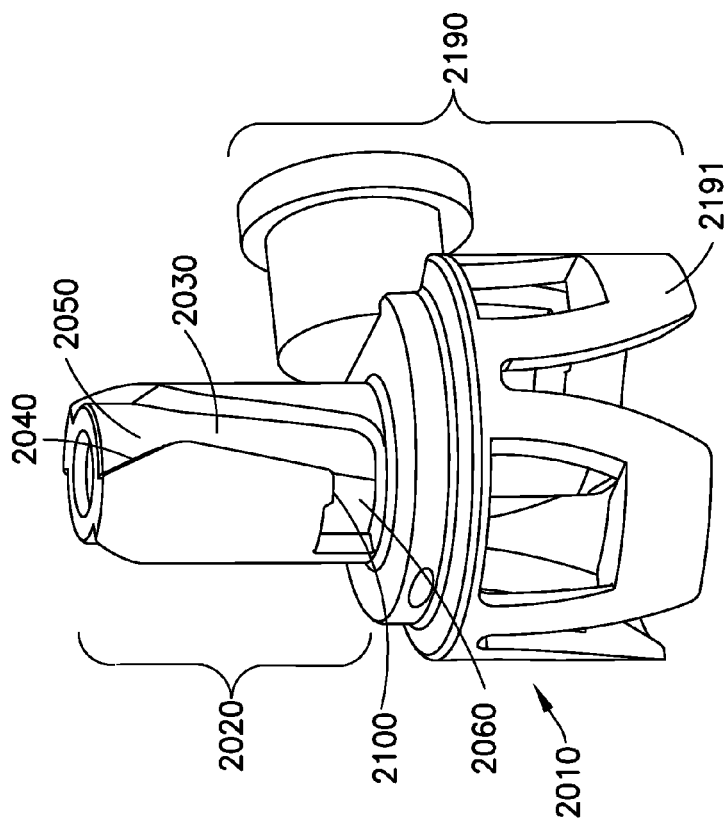
FIG. 22 is a perspective view of a vial adapter according to a second aspect of the present invention.
Figure 24:
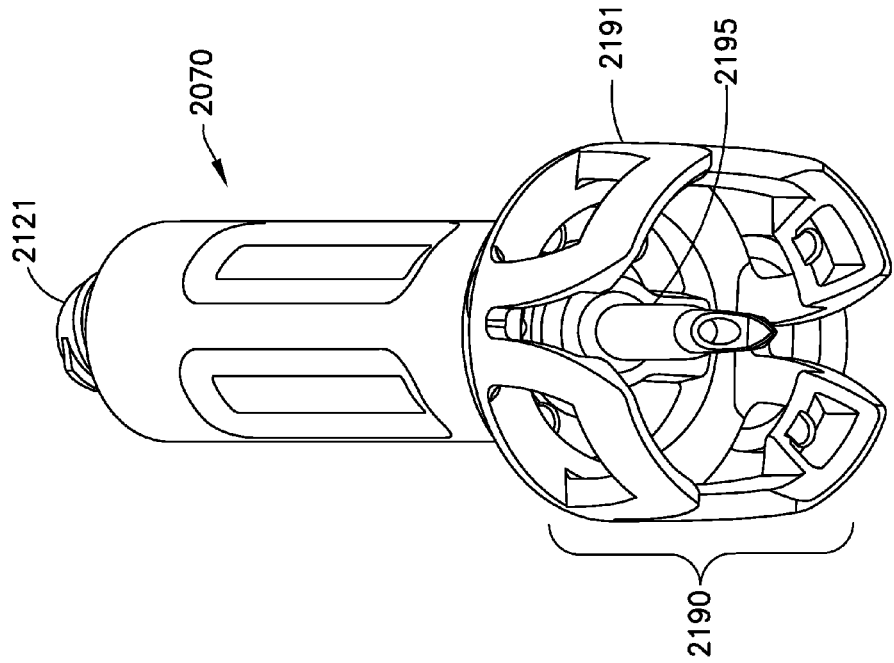
FIG. 24 is a bottom perspective view of the syringe adapter of FIG. 22 and the vial adapter of FIG. 22, showing the syringe adapter connected to the vial adapter.

Turning to FIGS. 23 and 24, shown are front and perspective views of the first connection member 2010 of a non-limiting aspect of the present invention mated to a second connection member 2070 that is embodied as a syringe adapter. Connection of first 2010 and second 2070 connection members allows for formation of a fluid channel therebetween, and reconstitution, aspiration, and delivery of compounds. Elements of the connection are substantially similar to the elements described in detail previously, except for the shape of channel 2030 and shoulder 2040 of the first connection member 2010, and include association of surfaces 2026 and 2081 of first and second connection members 2010 and 2070, respectively. As with other aspects, arms 2191 of vial attachment 2190 can encircle a vial and allow for needle 2195 to pierce vial for delivery and/or withdrawal of liquids.

Figure 25:
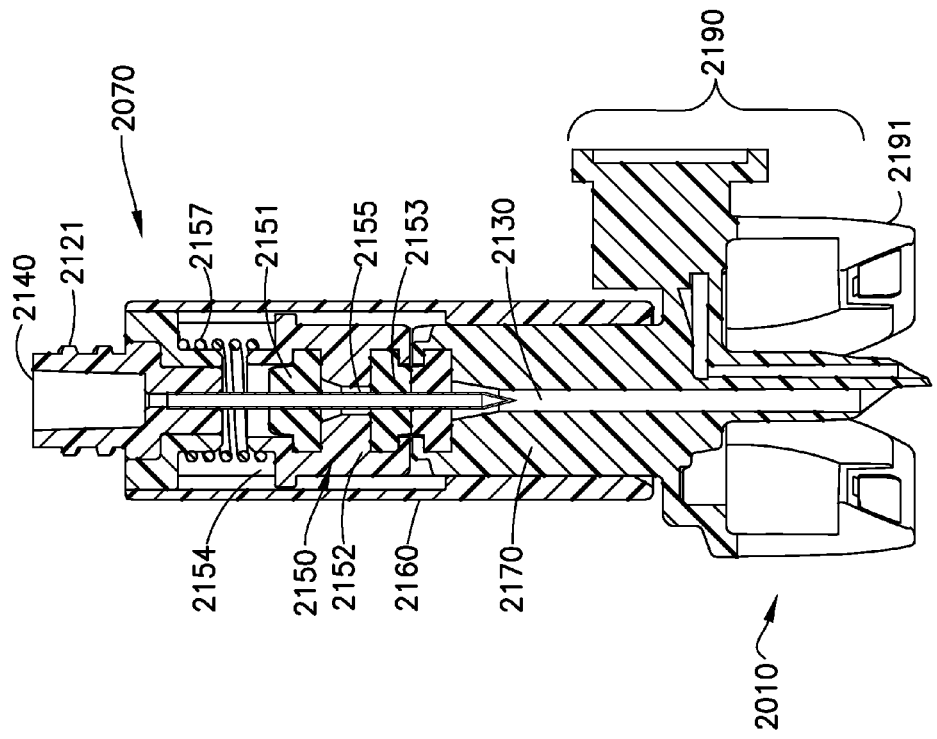
FIG. 25 is a cross-sectional view of the syringe adapter of FIG. 22 and the vial adapter of FIG. 22, showing the syringe adapter connected to the vial adapter.

Turning to FIG. 25, a cross-sectional view of first connection member 2010 mated to second connection member 2070 is shown. Second connection member 2070 has first and second ends, sidewalls 2160 defining a hollow portion 2170, and protrusion for mating with first connection member 2010. In the non-limiting aspect shown in FIG. 25, second connection member 2070 includes as a second end a syringe adapter. Syringe adapter includes luer lock 2121 for mating with any type of syringe. Those of skill in the art will appreciate that luer locks can be used to mate the syringe adapter with any type of syringe having a luer lock. With reference to FIG. 25, the syringe adapter includes a male luer lock 2121, which can be mated with any typical female luer lock (not shown).

Second connection member 2070 includes fluid channel 2140 and, in non-limiting aspects, includes seal or membrane apparatus 2150. The seal or membrane apparatus 2150 is configured to form a fluid-tight seal in the fluid channel 2140. Seal or membrane apparatus 2150 can form a fluid-tight seal in second connection member 2070 alone, or may form a seal for both fluid channel 2140 and a fluid channel 2130 of a first connection member 2010 when the second connection member 2070 is mated to first connection member 2010. Seal or membrane apparatus 2150 may also be a part of first connection member 2010.

In non-limiting aspects, seal or membrane apparatus 2150 may be self-healing, for example such that when a needle 2155 is included with second connection member 2070 in aspects in which second connection member 2070 includes a syringe adapter and first connection member 2010 includes a vial attachment 2190, a user or healthcare practitioner reconstituting the compound in the vial actuates the syringe and the needle pierces seal or membrane apparatus 2150. When the compound is reconstituted and the drug is to be withdrawn into the syringe, conclusion of that process can result in the syringe retracting through seal or membrane apparatus 2150, restoring a fluid tight seal and preventing exposure of the user or healthcare practitioner to the compound.

In non-limiting aspects, seal or membrane apparatus 2150 may be also be a multi-component seal or membrane. For example, in the aspect illustrated in FIG. 25, seal 2150 is made up of three separate components, 2151, 2152, and 2153. Portion of seal 2151 may be a compliant, self-healing membrane in which a needle 2155 may be embedded. The compliant nature of the seal allows for a fluid-tight seal to be formed between the chamber 2154 passing through the primary seal 2152 and the chamber in which the majority of the needle 2155 is located. Third portion of seal 2153 is also self-healing, and maintains the chamber 2154 in isolation from the fluid channel 2140. A user or healthcare practitioner reconstituting the compound in the vial actuates the syringe and the needle pierces seal 2153. When the compound is reconstituted and the drug is to be withdrawn into the syringe, conclusion of that process can result in the syringe retracting through seal or membrane 2153 and into chamber 2154, restoring a fluid tight seal and preventing exposure of the user or healthcare practitioner to the compound. Maintenance of the syringe between two fluid-tight seals 2151, 2153 provides further protection for a user.

Seals or membranes suitable for use with the present invention in the aspect shown in FIG. 25 and described above, or with a singular self-healing seal or membrane, are well-known to those in the art and allow penetration by a point, i.e., needle, such that upon withdrawal of the point, the seal substantially reseals to preclude fluid passage. Suitable materials for the seals are well known in the art and should be selected based on the intended use for the device such as biocompatibility, chemically inert, and compatible with any chemical reagents or treatments contained therein, be FDA and/or OSHA approved, and suitable for use in CSTDs. Such seals may be formed out of natural materials such as rubber, synthetic polymers, and/or silicone, such as room temperature vulcanizing silicone.

Referring to FIGS. 26A-26E, further aspects of the protrusion 90 of the second connection member 70 are provided. Although the protrusion 90 shown in FIGS. 1-25 is generally circular or semi-spherical, the protrusion 90 may have any suitable shape that is configured to be received within the channel 30 of the first connection member 10. In particular, as shown in FIGS. 26A-26E, the protrusion 90 may be circle-shaped, oblong-shaped, diamond-shaped, square-shaped, or rectangle-shaped. Each of these shapes may be utilized with the channel 30 and notch 100 shown in FIG. 2 or the channel 30 and notches 110, 120 shown in FIGS. 7A and 7B and where the protrusion 90 has a clearance arrangement into the notches 100, 110, 120 or a frictional engagement into the notches 100, 110, 120. The square-shaped and rectangle-shaped protrusions 90 may be particularly suited for the clearance arrangements to ensure a secure engagement within the notches 100, 110, 120.

While the present invention is described with reference to several distinct aspects of a connection apparatus for a CSTD and methods of use thereof, those skilled in the art may make modifications and alterations without departing from the scope and spirit of the invention. Accordingly, the above detailed description is intended to be illustrative rather than restrictive.

The invention claimed is:

1. A connection apparatus for a medical device comprising:
    a first connection member having a first end and a second end, the first connection member defining at least one channel adjacent the first end, the at least one channel having a first portion extending in an axial direction, a second portion extending in a transverse direction relative to the axial direction, and a third portion extending between the first portion and the second portion, the second portion of the at least one channel defining a terminus, the at least one channel having a shoulder adjacent to the first end of the first connection member that defines a channel entry, the first connection member having a curved wall that defines a portion of the first portion and the third portion of the at least one channel, the curved wall is curved from the channel entry to the second portion of the at least one channel; and
    a second connection member having a first end and a second end, the second connection member having at least one protrusion adjacent the first end,
    wherein when the at least one protrusion of the second connection member enters the at least one channel of the first connection member, axial movement of the second connection member towards the first connection member causes engagement of the at least one protrusion with the curved wall and at least one of the first and second connection members to rotate relative to the other connection member to enter a locked state where the at least one protrusion reaches the terminus of the second portion of the at least one channel, wherein the shoulder is configured to guide the at least one protrusion of the second connection member into the channel entry regardless of the orientation of the at least one protrusion relative to the channel entry.

2. The connection apparatus of claim 1, wherein the channel entry is wider than the first portion of the at least one channel and the second portion of the at least one channel.

3. The connection apparatus of claim 1, wherein the second portion of the at least one channel comprises a notch extending in the axial direction.

4. The connection apparatus of claim 3, wherein the notch extends towards the first end of the first connection member.

5. The connection apparatus of claim 3, wherein the notch extends towards the second end of the first connection member relative to the second portion of the at least one channel.

6. The connection apparatus of claim 3, wherein the at least one protrusion forms a positive lock with the notch to removably secure the first connection member to the second connection member when the first and second connection members are in the locked state.

7. The connection apparatus of claim 1, wherein the second portion of the at least one channel comprises a substantially axial notch extending distally and a substantially axial notch extending proximally relative to the first end of the first connection member.

8. The connection apparatus of claim 1, wherein the first and second connection members further comprise fluid channels therethrough such that when the first connection member and second connection member are mated, the fluid channels form a fluid path.

9. The connection apparatus of claim 8, wherein at least one of the first connection member and second connection member further comprises a self-healing membrane in the respective fluid channel and wherein when the first connection member is mated with the second connection member, the self-healing membrane forms a fluid-tight seal.

10. The connection apparatus of claim 1, further comprising an indicator of the locked state between the first connection member and the second connection member.

11. The connection apparatus of claim 10, wherein the indicator is a visual indicator.

12. The connection apparatus of claim 11, wherein the first and second connection members each comprise a flat portion and a rounded portion, the visual indicator comprising alignment of the flat portion of the first connection member with the flat portion of the second connection member and the alignment of the round portion of the first connection member with the round portion of the second connection member.

13. The connection apparatus of claim 10, wherein the indicator is a tactile indicator, and wherein the interaction of the at least one protrusion with a notch provides tactile indication of the locked state.

14. The connection apparatus of claim 1, wherein the first end of the second connection member comprises sidewalls enclosing a hollow portion, the sidewalls extending axially away from the second end of the second connection member, and wherein the sidewalls include the at least one protrusion, the at least one protrusion extending inward.

15. The connection apparatus of claim 1, wherein one of the first connection member and second connection member is provided on a syringe adapter and the other connection member is provided on at least one of a vial adapter and a patient connector.

16. The connection apparatus of claim 1, wherein the shoulder is rounded and the first portion and the third portion of the at least one channel define a non-linear path.

17. A connection apparatus for a medical device comprising:
a first connection member having a first end and a second end, the first connection member defining at least one channel adjacent the first end, the at least one channel having a first portion extending from a position adjacent the first end of the first connection member toward the second end of the first connection member, a second portion extending in a transverse direction relative to the first portion, and a third portion extending between the first portion and the second portion, the at least one channel having a shoulder adjacent to the first end of the first connection member that defines a channel entry, the first connection member having a first wall that defines a portion of the first portion and the third portion of the at least one channel, the first wall extends along a non-linear path on the first connection member from the first end of the first connection member to the second portion of the at least one channel, the first connection member having a second wall that extends along a non-linear path on the connection member from the first end of the first connection member to the third portion of the at least one channel and extends along a non-linear path on the first connection member from the third portion to the second portion of the at least one channel; and
a second connection member having a first end and a second end, the second connection member having at least one protrusion adjacent the first end,
wherein the at least one protrusion of the second connection member is configured to be received by the at least one channel of the first connection member, the first connection member and the second connection member having a locked state where the first connection member is secured to the second connection member, the at least one protrusion of the second connection member positioned in the second portion of the at least one channel of the first connection member when the first and second connection members are in the locked state, and wherein the channel entry is wider than the first portion of the at least one channel of the first connection member.

18. The connection apparatus of claim 17, wherein the second portion of the at least one channel of the first connection member extends in a transverse direction relative to a longitudinal axis of the first connection member.

19. The connection apparatus of claim 17, wherein the second portion of the at least one channel comprises a notch extending in an axial direction.

* * * * *